(12) United States Patent
Seong et al.

(10) Patent No.: US 10,030,226 B2
(45) Date of Patent: Jul. 24, 2018

(54) INDUCED REGULATORY T CELL AND USE THEREOF

(71) Applicant: SEOUL NATIONAL UNIVERSITY R&DB FOUNDATION, Seoul (KR)

(72) Inventors: Rho Hyun Seong, Seongnam-si (KR); Sung Kyu Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 14/747,442

(22) Filed: Jun. 23, 2015

(65) Prior Publication Data
US 2015/0368611 A1 Dec. 24, 2015

(30) Foreign Application Priority Data
Jun. 24, 2014 (KR) ........................ 10-2014-0077098

(51) Int. Cl.
| | | |
|---|---|---|
| C12N 5/10 | (2006.01) | |
| C12N 15/63 | (2006.01) | |
| C12N 5/0783 | (2010.01) | |
| A61K 35/17 | (2015.01) | |

(52) U.S. Cl.
CPC ............ *C12N 5/0637* (2013.01); *A61K 35/17* (2013.01); *C12N 2501/15* (2013.01); *C12N 2510/00* (2013.01)

(58) Field of Classification Search
None
See application file for complete search history.

(56) References Cited

U.S. PATENT DOCUMENTS

| | | |
|---|---|---|
| 7,579,318 B2 | 8/2009 | Divita et al. |
| 8,044,019 B2 | 10/2011 | Uno et al. |
| 8,614,194 B1 | 12/2013 | Chen et al. |
| 8,859,507 B2 | 10/2014 | Lee |
| 2003/0054007 A1 | 3/2003 | Felgner et al. |
| 2011/0189159 A1 | 8/2011 | Chatterjee et al. |
| 2013/0035333 A1 | 2/2013 | Mold |
| 2013/0071409 A1 | 3/2013 | Riley et al. |

FOREIGN PATENT DOCUMENTS

| | | |
|---|---|---|
| EP | 0 506 884 B1 | 9/1996 |
| EP | 1 676 588 A1 | 7/2006 |
| EP | 2 090 584 A1 | 8/2009 |
| WO | 2013/098337 A1 | 7/2013 |
| WO | 2014/041505 A1 | 3/2014 |
| WO | 2014/056813 A1 | 4/2014 |

OTHER PUBLICATIONS

Pan et al, CCAAT/Enhancer-binding Protein Activates the CD14 Promoter and Mediates Transforming Growth Factor b Signaling in Monocyte Development, JBC, 1999, pp. 23242-23248.*
Shimatani et al, PD-1+ memory phenotype CD4+ T cells expressing /EBPa underlie T cell immunodepression in sensecence and leukemia, PNAS, 2009, p. 15807-15812.*
Walker et al, Induction of FoxP3 and acquisition of T regulatory activity by stimulated human CD4+CD25—T cells, The Journal of Clinical Investigation, Nov. 2003, vol. 112(9), pp. 1437-1443.*
Mussbach et al, Transduct ion of Peptides and Proteins Into Live Cells by Cell Penetrating Peptides, Journal of Cellular Biochemistry 112:3824-3833 (2011).*
Fumoto et al, Targeted Gene Delivery: Importance of Adminstration Routes, CHpater !, 2013, Intech, pages.*
Knosp et al., "Regulation of Foxp3+ Inducible Regulatory T Cell Stability by SOCS2", J Immunol, vol. 190, pp. 3235-3245, (2013), pre-published online Mar. 1, 2013.
"Control of regulatory T and TH17 cell differentiation by CCAAT/enhancer binding protein", http://www.riss.kr/link?id=T13141934, retrieved Nov. 5, 2014, (2013).
Chatterjee et al., "Suppression of the C/EBP family of transcription factors in adipose tissue causes lipodystrophy", Journal of Molecular Endocrinology, vol. 46, pp. 175-192, (2011).
Chen et al., "Conversion of Peripheral CD4+CD25—Naive T Cells to CD4+CD25+ Regulatory T Cells by TGF-β Induction of Transcription Factor Foxp3", The Journal of Experimental Medicine, vol. 198, No. 12, pp. 1875-1886, (2003).
Elias et al., "Retinoic acid inhibits Th17 polarization and enhances FoxP3 expression through a Stat-3/Stat-5 independent signaling pathway", Blood, vol. 111, pp. 1013-1020, (2008).
Floess et al., "Epigenetic Control of the foxp3 Locus in Regulatory T Cells", PLoS Biology, vol. 5, Issue 2, p. e38 (0169-0178), (2007).
Mucida et al., "Reciprocal TH17 and Regulatory T Cell Differentiation Mediated by Retinoic Acid", Science, vol. 317, pp. 256-260, (2007).
Ohoka et al., "The Orphan Nuclear Receptor RORα Restrains Adipocyte Differentiation through a Reduction of C/EBPβ Activity and Perilipin Gene Expression", Molecular Endocrinology, vol. 23, pp. 759-771, (2009).
Orzechowska et al., "Controlled delivery of BID protein fused with TAT peptide sensitizes cancer cells to apoptosis", BMC Cancer, vol. 14, pp. 771 (1-13), (2014).
Polansky et al., "DNA methylation controls Foxp3 gene expression", Eur. J. Immunol., vol. 38, pp. 1654-1663, (2008).
Ron et al., "CHOP, a novel developmentally regulated nuclear protein that dimerizes with transcription factors C/EBP and LAP and functions as a dominant-negative inhibitor of gene transcription", Genes Dev., vol. 6, pp. 439-453, (1992).
Ruczynski et al., "Cell-penetrating peptides as a promising tool for delivery of various molecules into the cells", Folia Histochemica et Cytobiologica, vol. 52, No. 4, pp. 257-269, (2014).

(Continued)

*Primary Examiner* — Maria Marvich
(74) *Attorney, Agent, or Firm* — Vorys, Sater, Seymour & Pease LLP; Mih Suhn Koh

(57) ABSTRACT

The present invention relates to a transduced T cell precursor prepared by introducing a gene construct comprising a polynucleotide encoding C/EBP (CCAAT/enhancer binding protein) to a T cell precursor and overexpressing the C/EBP thereby, wherein the transduced T cell precursor is capable of differentiating into a regulatory T cell and an induced regulatory T cell differentiated therefrom. The transduced T cell precursor and the induced regulatory T cell may be useful for preventing and treating autoimmune diseases, inflammatory diseases and graft rejections caused by the malfunction of immune response.

6 Claims, 19 Drawing Sheets

(56) References Cited

OTHER PUBLICATIONS

Xiao et al., "Retinoic Acid Increases Foxp3+ Regulatory T Cells and Inhibits Development of Th17 Cells by Enhancing TGF-β-Driven Smad3 Signaling and Inhibiting IL-6 and IL-23 Receptor Expression", J. Immunol., vol. 181, pp. 2277-2284, (2008).
Bettelli et al., "Reciprocal developmental pathways for the generation of pathogenic effector TH17 and regulatory T cells", Nature, vol. 441, pp. 235-238, (2006).
Tsukada et al., "The CCAAT/enhancer (C/EBP) family of basic-leucine zipper (bZIP) transcription factors is a multifaceted highly-regulated system for gene regulation", Cytokine, vol. 54, pp. 6-19, (2011).
Fontenot et al., "Foxp3 programs the development and function of CD4+CD25+ regulatory T cells", Nature Immunology, vol. 4, No. 4, pp. 330-336, (2003).
Williams et al., "C/EBP proteins contain nuclear localization signals imbedded in their basic regions.", Gene Expr., vol. 6, No. 6, pp. 371-385, (1997). (Abstract only).
Ma et al., "Enhanced Peptide Delivery into Cells by Using the Synergistic Effects of a Cell-Penetrating Peptide and a Chemical Drug to Alter Cell Permeability", Mol. Pharmaceutics, vol. 12, No. 6, pp. 2040-2048, (2015).
Huehn et al., "Epigenetic control of FOXP3 expression: the key to a stable regulatory T-cell lineage?", Nature Reviews: Immunology, vol. 9, pp. 83-89, (2009).
Zheng et al., "Role of conserved non-coding DNA elements in the Foxp3 gene in regulatory T-cell fate", Nature, vol. 463, pp. 808-812, (2010).
Poli et al., "IL-6DBP, a Nuclear Protein Involved in Interleukin-6 Signal Transduction, Defines a New Family of Leucine Zipper Proteins Related to C/EBP", Cell, vol. 63, pp. 643-653, (1990).

\* cited by examiner

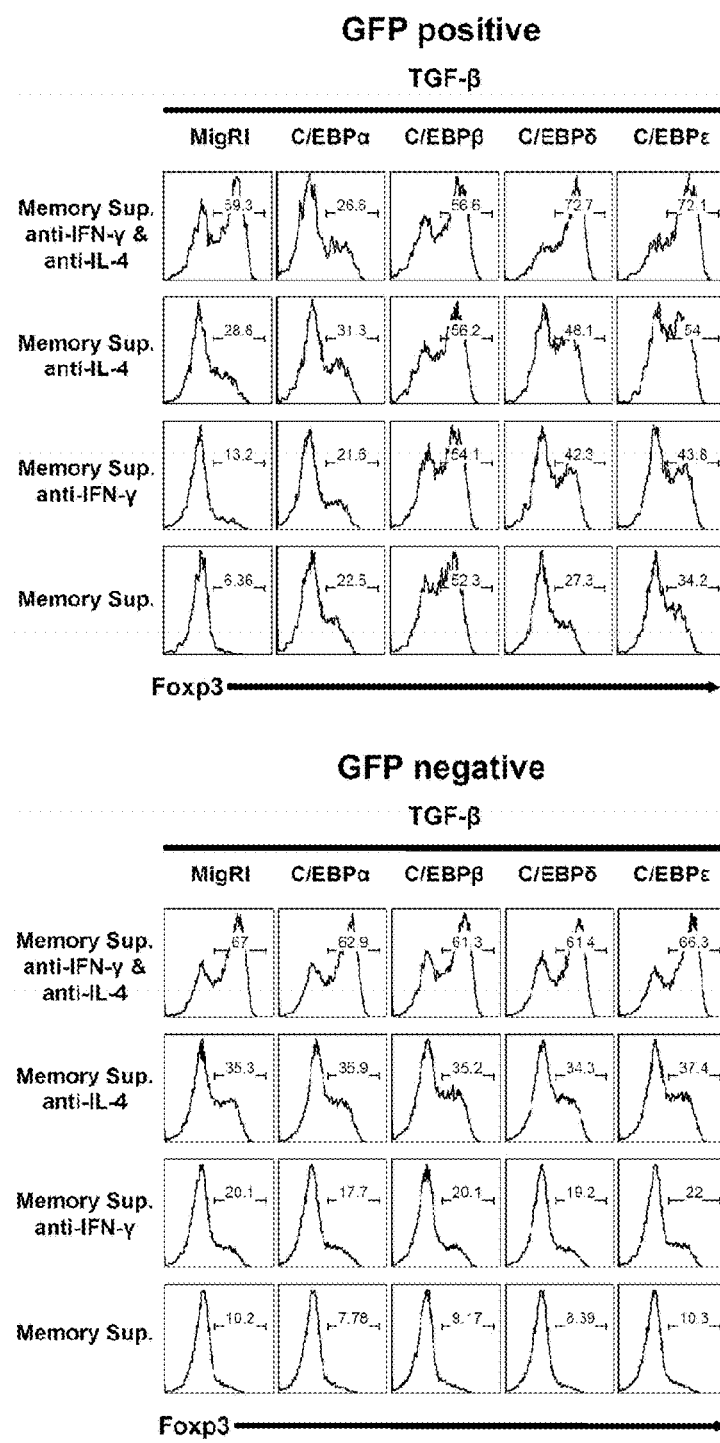

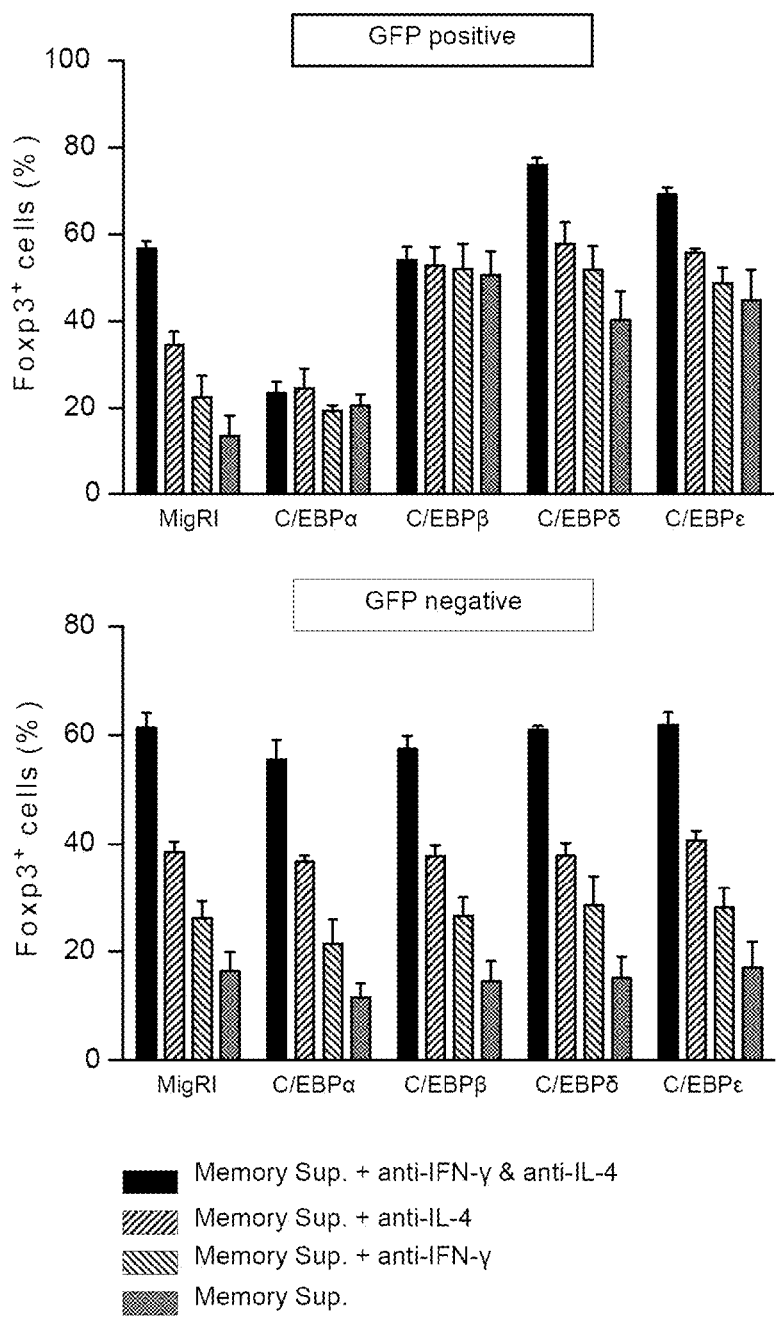

INDUCED REGULATORY T CELL AND USE THEREOF

The Sequence Listing submitted in text format (.txt) filed on Aug. 15, 2016, named "SequenceListing.txt", created on Aug. 15, 2016, 4.2 KB), is incorporated herein by reference.

CROSS REFERENCES

This application claims the benefit of Korean Patent Application Nos. 10-2014-0077098 filed Jun. 24, 2014, the contents of which are incorporated herein by reference.

TECHNICAL FIELD

The present invention relates to a novel cell and use thereof, more particularly to an induced regulatory T cell and use thereof.

BACKGROUND OF THE INVENTION

According to recent studies, it has been proven that two kinds of cells, regulatory T ($T_{reg}$) cells and T helper 17 ($T_H17$) cells, which belong to CD4$^+$ T lymphocytes, play important role in autoimmune diseases. These two cells have been known to differentiate from common precursor cells, i.e., naïve CD4$^+$ T cells under the influence of a cytokine, a transforming growth factor beta 1 (TGFβ1) (Bettelli, E., Nature, 441: 235-238, 2006). However, $T_{reg}$ cells inhibit the function of abnormally activated immune cells and play important role in immunological tolerance, and $T_H17$ cells, which are inflammatory T cells expressing IL-17, accelerate progress of the autoimmune diseases by maximizing signals of inflammation reaction.

Therefore, the development of therapeutic agents aiming the suppression of $T_H17$ cell activity has been given attention for treating autoimmune diseases not regulated by $T_{reg}$ cells.

US20130071409A discloses a therapeutic agent for treating autoimmune diseases through the regulation of $T_H17$ cells using ICOS (inducible costimulatory, CD278). US20130035333A relates to use of cinnabarinic acid as a modulator of immune responses in autoimmune disorders and discloses a method of treating through the regulation of aryl hydrocarbon receptor activity.

However, it is needed to develop a therapeutic agent for treating disorders related to immune response and inflammation based on the regulation of differentiation of CD4$^+$ T cells into $T_{reg}$ cells and the stabilization of the differentiated $T_{reg}$ cells considering the roles of $T_{reg}$ cells and $T_H17$ cells during the development of the immune system.

Technical Problems

The present invention has been made to provide an induced regulatory T cell induced by genetic manipulation and a cell-based therapeutic agent for treating immune diseases based thereon.

SUMMARY OF THE INVENTION

In an aspect of the present invention, a transduced T cell precursor prepared by introducing a gene construct comprising a polynucleotide encoding C/EBP (CCAAT/enhancer binding protein) to a T cell precursor and overexpressing the C/EBP thereby, wherein the transduced T cell precursor is capable of differentiating into a regulatory T cell is provided.

According to the transduced T cell precursor, the T cell precursor may be a CD4$^+$ cell and the CD4$^+$ cell may be a naïve T cell, a memory T cell or an effector T cell.

In another aspect of the present invention, an induced regulatory T cell ($iT_{reg}$) prepared by introducing a gene construct comprising a polynucleotide encoding C/EBP to a T cell precursor and overexpressing the C/EBP thereby is provided. The transduced T cell precursor may be Foxp3-positive.

According to the induced regulatory T cell, the T cell precursor may be a CD4$^+$ cell and the CD4$^+$ cell may be a naïve T cell, a memory T cell or an effector T cell.

According to the induced regulatory T cell, the T cell precursor may be further treated with transforming growth factor-beta (TGFβ).

The C/EBP used in accordance with an embodiment of the present invention may be one of various natural or synthetic C/EBPs (CCAAT/enhancer binding proteins) showing biological effect according to an embodiment of the present invention and one or more among α, β, δ and ε may be used. In an embodiment of the present invention C/EBPβ is used.

The induced regulatory T cell may be prepared by withdrawing the suppression of Foxp3 (forkhead box P3) expression due to C/EBP expressed by a transgene encoding C/EBP which is introduced to a T cell precursor, but not limited thereto. In this case, the suppression of Foxp3 expression is due to an inhibitory cytokine. The inhibitory cytokine may be INF-γ and/or IL-4.

The withdrawing the suppression of Foxp3 expression by C/EBP in accordance with an embodiment of the present invention may be accomplished by binding of the C/EBP to a methylated CpG dinucleotide located in the $T_{reg}$-specific demethylated region (TSDR) of Foxp3 locus.

In an aspect of the present invention, a stabilized regulatory T cell prepared by introducing a gene construct comprising a polynucleotide encoding C/EBP to a regulatory T cell and overexpressing the C/EBP thereby is provided.

In an aspect of the present invention, a composition comprising one cell or at least two cells selected from the group consisting of the transduced T cell precursor, the induced regulatory T cell and a transfected regulatory T cell prepared by transfecting a regulatory T cell with a gene construct comprising a polynucleotide encoding C/EBP and overexpressing the C/EBP thereby is provided. The composition may be used for treating or preventing various immune related disorders that require the function of regulatory T cells. For example, the composition may be used for treating or preventing autoimmune diseases, inflammatory disorders, or graft rejections of cells, tissues or organs, but not limited thereto. In addition, the composition may further comprise one or more pharmaceutically accepted carriers.

In another aspect of the present invention, a cell therapy agent for treating immune-related disorder comprising one cell or at least two cells selected from the group consisting of the transduced T cell precursor, the induced regulatory T cell and a transfected regulatory T cell prepared by transfecting a gene construct comprising a polynucleotide encoding C/EBP and overexpressing the C/EBP thereby, and which is Foxp3-positive as an active ingredient is provided.

Due to the overexpression of C/EBP in accordance with an embodiment of the present invention, the naïve T cell, the memory T cell or the effector T cell may be differentiated into an induced regulatory T cell and the induced regulatory T cell may be stabilized and thus may be used for treating or preventing immune-related disorders.

The T cell precursor or the induced regulatory T cell may be an autologous cell, an allograft cell or a xenograft cell. The cell-based medicine in accordance with an embodiment of the present invention may be used as ex vivo method comprising extracting T cells from a subject and preparing C/EBP-overexpressing cells by introducing C/EBP to the extracted T cells and then injecting the C/EBP-overexpressing cells to the subject, but not limited thereto.

In another aspect of the present invention, a method of treating a subject suffering from an autoimmune disease comprising administrating a therapeutic effective amount of one cell or at least two cells selected from the group consisting of the transduced T cell precursor, the induced regulatory T cell and a stabilized regulatory T cell prepared by introducing a gene construct comprising a polynucleotide encoding C/EBP to a regulatory T cell and overexpressing the C/EBP thereby in the cell to the subject.

According to the method, the administrating may be injecting or transplanting the cell or cells to the site (e.g., cells, tissues and organs) where the disease occurs, and any conventional administration methods such as intravenous injection, intramuscular injection, subcutaneous injection and intraperitoneal injection, etc. may be used, but not limited thereto.

In an aspect of the present invention, a method of differentiating a T cell precursor into a regulatory T cell comprising: delivering C/EBP to nucleus of a T cell precursor; or introducing a gene construct including a heterologous polynucleotide encoding the C/EBP to the T cell precursor and overexpressing the C/EBP in the T cell precursor thereby is provided.

In an aspect of the present invention, a method of stabilizing a regulatory T cell comprising delivering C/EBP to nucleus of a regulatory T cell; or introducing a gene construct including a heterologous polynucleotide encoding the C/EBP to the regulatory T cell and overexpressing the C/EBP in the regulatory T cell thereby is provided. According to the method, the regulatory T cell may be an induced regulatory T cell or a natural regulatory T cell.

The method may further comprise treating TGFβ to the regulatory T cell, in order to promote the stabilization of the regulatory T cell.

In an aspect of the present invention, a method of suppressing differentiation of a T cell precursor into a $T_H17$ cell comprising: delivering C/EBP to nucleus of a T cell precursor; or introducing a gene construct including a heterologous polynucleotide encoding the C/EBP to the T cell precursor and overexpressing the C/EBP in the T cell precursor thereby is provided.

The method may further comprise treating TGFβ to the T cell precursor, in order to inhibit differentiation of the T cell precursor into the $T_H17$ cell.

The transduced T cell precursor, the induced regulatory T cell or the stabilized regulatory T cell may be proliferated maintaining their properties as well as inhibiting differentiation into $T_H17$ cells and thus mass production of those cells may be accomplished. The cells of the present invention may be useful for treating and preventing immune diseases such as autoimmune disease, inflammatory disease and graft rejection caused by immune responses.

BRIEF DESCRIPTION OF DRAWINGS

FIG. 1A represents quantitative RT-PCR analysis of C/EBPβ mRNA in $CD4^+$ naïve T cells inactivated (0 hr) or stimulated with anti-CD3 and anti-CD28 for 24 hr under conditions as indicated. Data are representative of two independent experiments with consistent results and normalized with β-actin (mean and s.e.m. of triplicates). FIG. 1B is an image representing results of immunoblot analysis of C/EBPβ in the nuclear fraction of naïve $CD4^+$ T cells stimulated as in FIG. 1A. FIG. 1C represents flow cytometry of intracellular staining for Foxp3 in $CD4^+$ naïve T cells infected with control retrovirus (MigRI) or retrovirus encoding A-C/EBP or C/EBPζ and stimulated with anti-CD3 and anti-CD28 for 2 d in the presence of TGF-β and memory supernatant with DMSO (top) or ATRA (bottom) (left panel). Anti-IFN-γ and anti-IL-4 antibodies were added (right panel). Histograms are gated for $GFP^+$ cells. Numbers indicate percent $Foxp3^+$ cells in $GFP^+$ gate. FIG. 1D is a graph representing the frequency of $Foxp3^+$ cells in FIG. 1C. FIG. 1E represent flow cytometry of intracellular staining for Foxp3 in $CD4^+$ naïve T cells infected with control retrovirus (MigRI) or retrovirus encoding A-C/EBP or C/EBPζ and stimulated with anti-CD3 and anti-CD28 for 2 d in the presence of TGF-β, IL-2, IFN-γ and IL-4 with DMSO (top) or ATRA (bottom) (left panel). Anti-IFN-γ and anti-IL-4 antibodies were added (right panel). Histograms are gated for $GFP^+$ cells. Numbers indicate percent $Foxp3^+$ cells in $GFP^+$ gate. FIG. 1F is a graph representing the frequency of $Foxp3^+$ cells in FIG. 1E.

FIG. 2A represents flow cytometry of intracellular staining for Foxp3 in $CD4^+$ naïve T cells infected with control retrovirus (MigRI) or retrovirus encoding C/EBPβ and stimulated with anti-CD3 and anti-CD28 for 2 d in the presence of TGF-β and memory supernatant with anti-IFN-γ and anti-IL-4 Abs, anti-IL-4 Ab, anti-IFN-γ Ab, or none. Histograms are gated for $GFP^+$ cells. Numbers indicate percent $Foxp3^+$ cells in $GFP^+$ gate (left panel). FIG. 2B represents the frequency of $Foxp3^+$ cells from four independent experiments (right panel, mean and s.e.m). FIG. 2C represents flow cytometry of intracellular staining for Foxp3 in $CD4^+$ naïve T cells infected with control retrovirus (MigRI) or retrovirus encoding C/EBPβ and stimulated with anti-CD3 and anti-CD28 for 2 d in the presence of TGF-β and IL-2 with anti-IFN-γ and anti-IL-4 Abs, IFN-γ and anti-IL-4 Ab, IL-4 and anti-IFN-γ Ab, or IFN-γ and IL-4. Histograms are gated for $GFP^+$ cells. Numbers indicate percent $Foxp3^+$ cells in $GFP^+$ gate (left panel). FIG. 2D represents the frequency of $Foxp3^+$ cells from three independent experiments (right panel, mean and s.e.m). FIG. 2E represents quantitative RT-PCR analysis of FACS-sorted $GFP^-$ and $GFP^+$ cells from $CD4^+$ naïve T cells infected with control retrovirus (MigRI) or retrovirus encoding C/EBPβ and stimulated with anti-CD3 and anti-CD28 for 2 d in the presence of TGF-β and memory supernatant. Data are representative of two independent experiments with consistent results and normalized with β-actin (mean and s.e.m. of triplicates). FIG. 2F represents flow cytometry of sorted naïve $CD4^+$ ($CD4^+CD25^-Foxp3^-$) T cells from $Foxp3^{EGFP}$ mice infected with control retrovirus (MIN) or retrovirus encoding C/EBPβ (MIN-C/EBPβ) and stimulated with anti-CD3 and anti-CD28 for 2 d in the presence of TGF-β, IL-2, anti-IFN-γ and anti-IL-4 Abs. $GFP^+$ ($Foxp3^+$) $NGFR^+$ T cells were sorted to high purity (0 hr) and restimulated with anti-CD3 and anti-CD28 for 3 d in the presence of IL-2, anti-IFN-γ and anti-IL-4 Abs. Foxp3 expression was assessed based on GFP expression. Data are representative of two independent experiments with consistent results.

FIG. 3A is a graph representing body weight of RAG-2$^{-/-}$ mice after injecting 5×10$^5$ CD4$^+$CD45RB$^{high}$ cells alone (circular) or together with 2×10$^5$ FACS-sorted CD4$^+$GFP$^+$ cells infected with control retrovirus (MigRI) (squares) or retrovirus encoding C/EBPβ (triangles) and stimulated with anti-CD3 and anti-CD28 for 2 d in the presence of TGF-β and memory supernatant. Each time point contains three mice in each group. Data are representative of two independent experiments with consistent results. FIG. 3B is a photograph of spleens isolated from the mice of FIG. 3A. FIG. 3C is a series of photographs representing histological analysis of distal colon tissues of the mice stained with hematoxylin and eosin.

FIG. 4A represents a schematic diagram showing Foxp3 gene including exon-intron structure and regulatory elements thereof (top), and nucleotide sequence of Foxp3 TSDR (bottom, SEQ ID NO: 18) including 10 CpG motifs (underlined) and a CRE (boxed). FIG. 4B represents results of bisulfite sequencing of FACS-sorted GFP$^+$ cells from CD4$^+$ naïve T cells infected with control retrovirus (MigRI) or retrovirus encoding C/EBPβ and stimulated with anti-CD3 and anti-CD28 for 2 d in the presence of TGF-β and memory supernatant. FIG. 4C represents EMSA result of nuclear extracts of Jurkat cells transfected with control vector or C/EBPβ assessed with a probe covering the putative unmethylated or methylated CRE sequence in the Foxp3 TSDR region. FIG. 4D is a graph representing ChIP assay of C/EBPβ binding in the Foxp3 TSDR region in naïve CD4$^+$ T cells stimulated with anti-CD3 and anti-CD28 for 2 d in the presence of TGF-β, IL-2, IFN-γ and IL-4 with DMSO, ATRA, or ATRA plus 5-Aza. Cell lysates were immunoprecipitated with control IgG or anti-C/EBPβ antibody; results are presented as relative values to enrichment by immunoprecipitation with control IgG. Data are representative of two independent experiments with consistent results (mean and s.e.m. of triplicates). FIG. 4E represents flow cytometry of intracellular staining for Foxp3 in CD4$^+$ naïve T cells infected with control retrovirus (MigRI) or retrovirus encoding A-C/EBP or C/EBPζ and stimulated with anti-CD3 and anti-CD28 for 2 d in the presence of TGF-β, memory supernatant and ATRA with (bottom) or without (top) 5-aza. Histograms are gated for GFP$^+$ cells. Numbers indicate percent Foxp3$^+$ cells in GFP$^+$ gate (left panel). Frequency of Foxp3$^+$ cells (right panel). FIG. 4F represents Flow cytometry of intracellular staining for Foxp3 in CD4$^+$ naïve T cells infected with control retrovirus (MigRI) or retrovirus encoding A-C/EBP or C/EBPζ and stimulated with anti-CD3 and anti-CD28 for 2 d in the presence of TGF-β, IL-2, IFN-γ, IL-4 and ATRA with (bottom) or without (top) 5-aza. Histograms are gated for GFP$^+$ cells. Numbers indicate percent Foxp3$^+$ cells in GFP$^+$ gate (left panel). Frequency of Foxp3$^+$ cells (right panel).

FIG. 5A is a graph representing quantitative RT-PCR analysis of C/EBPβ mRNA in CD4$^+$ naïve T cells inactivated (0 hr) or stimulated with anti-CD3 and anti-CD28 for 24 hr under conditions as indicated. Data are representative of four independent experiments with consistent results and normalized with β-actin (mean and s.e.m. of triplicates). FIG. 5B represents flow cytometry of intracellular staining for Foxp3 in CD4$^+$ naïve T cells infected with control retrovirus (MigRI) or retrovirus encoding C/EBPβ and stimulated with anti-CD3 and anti-CD28 for 2 d in the presence of TGF-β, anti-IFN-γ and anti-IL4 Abs with (bottom) or without (top) IL-6. Histograms are gated for GFP$^+$ cells. Numbers indicate percent Foxp3$^+$ cells in GFP$^+$ gate (left panel). Frequency of Foxp3$^+$ cells from three independent experiments (right panel, mean and s.e.m). FIG. 5C represents flow cytometry of intracellular staining for Foxp3 in CD4$^+$ naïve T cells infected with control retrovirus (MigRI) or retrovirus encoding A-C/EBP or C/EBPζ and stimulated with anti-CD3 and anti-CD28 for 2 d in the presence of TGF-β, IL-6, anti-IFN-γ and anti-IL4 Abs with DMSO (top) or ATRA (bottom). Histograms are gated for GFP$^+$ cells. Numbers indicate percent Foxp3$^+$ cells in GFP$^+$ gate (left panel). Frequency of Foxp3$^+$ cells (right panel). FIG. 5D represents flow cytometry of intracellular staining for Foxp3 in CD4$^+$ naïve T cells co-transduced with retrovirus encoding C/EBPβ (MigRI vector:GFP reporter) and RORγt (MIN vector:NGFR reporter) and stimulated with anti-CD3 and anti-CD28 for 2 d in the presence of TGF-β and memory supernatant. Histograms are gated for GFP$^+$NGFR$^+$. Numbers indicate percent Foxp3$^+$ cells in GFP$^+$NGFR$^+$ gate. Data are representative of three independent experiments with consistent results. FIG. 5E represents co-immunoprecipation of C/EBPβ and RORγt from whole cell extracts of 293T cells. Cells were transfected with the indicated expression vectors.

FIG. 6A is flow cytometry of intracellular staining for IL-17A and Foxp3 in CD4$^+$ naïve T cells infected with control retrovirus (MigRI) or retrovirus encoding C/EBPβ and stimulated with anti-CD3 and anti-CD28 for 2 d in the presence of TGF-β, IL-6, anti-IFN-γ and anti-IL-4 Abs and then restimulated for 3 hr with PMA plus ionomycin. Plots are gated for GFP$^+$ cells. Numbers indicate percent cells in each quadrant (left panel), frequency of IL-17A$^+$ cells (right panel). FIG. 6B is a schematic diagram of mixed bone marrow transplantation. FIG. 6C represents flow cytometry of intracellular staining for IL-17A and Foxp3 in CD4$^+$ naïve T cells co-transduced with retrovirus encoding C/EBPβ and RORγt and stimulated with anti-CD3 and anti-CD28 for 2 d in the presence of anti-IFN-γ and anti-IL-4 Abs and then restimulated for 3 hr with PMA plus ionomycin. Plots are gated for GFP$^+$NGFR$^+$. Numbers indicate percent cells in each quadrant. Data are representative of two independent experiments with consistent results. FIG. 6D represents flow cytometry of intracellular staining for Foxp3 in CD4$^+$ naïve T cells co-transduced with retrovirus encoding C/EBPβ (MigRI vector:GFP reporter) and RORγt (MIN vector: NGFR reporter) and stimulated with anti-CD3 and anti-CD28 for 2 d in the presence of TGF-β and memory supernatant. Histograms are gated for GFP$^+$NGFR$^+$. Numbers indicate percent Foxp3$^+$ cells in GFP$^+$NGFR$^+$ gate. Data are representative of three independent experiments with consistent results. In FIGS. 6A, 6C, and 6D number represent 100 percentage of T cell. FIG. 6E is a graph representing luciferase assay of IL-17 promoter-CNS2 (conserved noncoding sequence 2) reporter. Jurkat cells were transfected with RORγt alone, RORγt plus C/EBPβ, or control vector alone with IL-17 promoter-CNS2 luciferase reporter vector. Luciferase reporter activities were normalized to that of an internal control (RSV-β-galactosidase activity). Background luciferase activities in cells transfected with control vector alone was set to 1. Data are representative of three independent experiments with consistent results (mean and s.e.m. of triplicate transfections). The result is independent experimental result of consistent two times (6C, 6D) and three times (6E), FIG. 6F represents EMSA of nuclear extracts of Jurkat cells transfected with RORγt alone or RORγt plus C/EBPβ and assessed with a probe covering ROR element (RORE) in IL-17 CNS2 region:lane 1, nuclear extracts from control-vector-transfected cells; lane 2, nuclear extracts from RORγt-transfected cells; lane 3, nuclear extracts as in lane 2 plus anti-RORγt antibody; lane 4, nuclear extracts from C/EBPβ and RORγt-co-transfected cells.

FIG. 7A represents flow cytometry of intracellular staining for Foxp3 in CD4$^+$ naïve T cells infected with control retrovirus (MigRI) or retrovirus encoding C/EBPα, C/EBPβ, C/EBPδ, or C/EBPε and stimulated with anti-CD3 and anti-CD28 for 2 d in the presence of TGF-β and memory supernatant with anti-IFN-γ and anti-IL-4 Abs, anti-IL-4 Ab, anti-IFN-γ Ab, or none. Histograms are gated for GFP$^+$ (left panel) and GFP$^-$ (right panel) cells. FIG. 7B is a series of graphs representing frequency of Foxp3$^+$ cells (mean and s.e.m of triplicate experiments).

FIG. 8A represents flow cytometry of intracellular staining for IL-17A and Foxp3 in CD4$^+$ naïve T cells infected with control retrovirus (MigRI) or retrovirus encoding C/EBPα, C/EBPβ, C/EBPδ, or C/EBPε and stimulated with anti-CD3 and anti-CD28 for 2 d in the presence of TGF-β, IL-6, anti-IFN-γ and anti-IL-4 Abs and then restimulated for 3 hr with PMA plus ionomycin. Plots are gated for GFP$^+$ (top) and GFP$^-$ (bottom) cells. Numbers in plots indicate percent cells in each quadrant. FIG. 8B is a graph representing the frequency of IL-17A$^+$ cells from three independent experiments.

DETAILED DESCRIPTION OF THE INVENTION

Figure 1A:
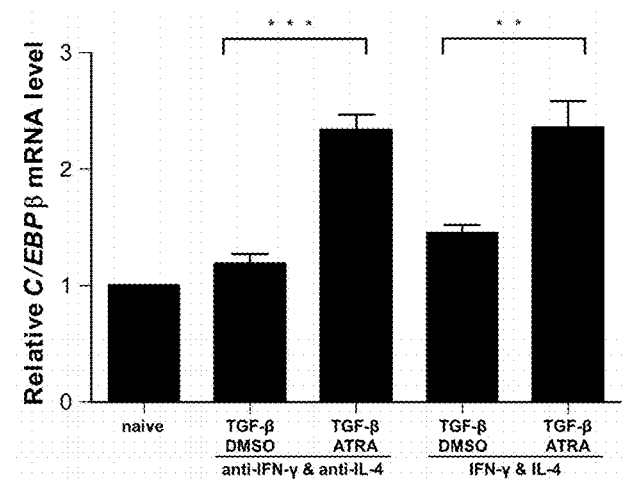
FIGS. 1A-1F represent that C/EBPβ acts in the presence of inhibitory cytokines in the downstream of retinoic acid (hereinafter, referred to 'RA')

The present invention is based on finding of novel function of C/EBPβ improving the differentiation and stabilization of regulatory T cells and suppressing the differentiation of $T_H17$ cells.

In an aspect of the present invention, a transduced T cell precursor prepared a transduced T cell precursor prepared by introducing a gene construct comprising a polynucleotide encoding C/EBP (CCAAT/enhancer binding protein) to a T cell precursor and overexpressing the C/EBP thereby, wherein the transduced T cell precursor is capable of differentiating into a regulatory T cell is provided.

The term "differentiation" used herein means the process by which a cell changes from one cell type to another.

The term "C/EBP" which is a type of transcription factor comprising a basic leucine zipper (bZIP) motif, means CCAAT/enhancer binding protein and includes 6 isotypes, C/EBPα, β, γ, δ, ε and ζ. In an embodiment of the present invention, isotypes α, β, δ, and ε may be used. Theses all C/EBP isotypes have considerable homology in the C-terminal including the bZIP motif (Tsukada, J. et al., Cytokine 54: 6-19, 2011). It has been known to play roles in energy metabolism, hematopoiesis, adipogenesis and the differentiation of osteoclast, but it has not been reported whether it plays role in regulating the differentiation of T cells.

Any known naturally isolated or synthesized proteins which belong to C/EBP family or genes encoding the same or functional equivalents thereof may be used as they have corresponding effects to the present invention. For example, cDNA of human C/EBPα is known as GenBank Accession No. NC_00019.9 (cDNA) and protein encoded by the cDNA is known as NCBI Reference Sequence No. NP_004355.2 and mouse C/EBPα is known as GenBank Accession No. NC_000068 (cDNA) and NCBI Reference Sequence No. NP_034013 (protein).

The term used herein "functional equivalents" means proteins or polynucleotides having substantially same quality with a wild type though they have additions, substitutions or deletions in the wild type sequence. For example, they include amino acid sequence variants in which some of amino acids among original amino acid sequence are substituted, deleted or added. In an embodiment, the amino acid substitution may be a conservative substitution in which the other similar amino acids are substituted for original amino acids, e.g., the substitution within aliphatic amino acids (Gly, Ala, and Pro), hydrophobic amino acids (Ile, Leu, and Val), aromatic amino acids (Phe, Tyr, and Trp), acidic amino acids (Asp and Glu), basic amino acids (His, Lys, Arg, Gln, and Asn) and sulfur-containing amino acids (Cys and Met). The deletion of amino acids is preferably localized in parts not directly involved in the function of C/EBP according to the present invention. In addition, the functional equivalents may also include fusion proteins prepared by fusing other proteins whose chemical structures are modified while maintaining basic structure and physiological activity of the C/EBP.

A polynucleotide encoding the C/EBP according to an embodiment of the present invention may be inserted into a vector or a gene construct. The polynucleotide according to an embodiment of the present invention may be isolated from nature or can be artificially synthesized or modified, one or more nucleotides may be modified by the substitution, deletion or addition, as the protein expressed by the modified polynucleotide has no significant change in its biological function, in particular in relation to the effects according to the present invention.

The vector including the polynucleotide according to the present invention may be one of various known expression vectors and the type thereof may be determined according to the host cell, the expression level, or the regulation of the expression, and a plasmid, a phage, a cosmid, a viral- or non-viral vector may be included but not limited thereto. The vector may exist as a self-replicable episome or be integrated into the host genomic DNA in order for protein expression. The vector may include expression regulatory elements such as promoter/enhancer and additional sequences needed for transcription, translation or processing. The expression regulatory elements may include constitutive elements as well as tissue-specific and/or inducible elements. In accordance with an embodiment of the present invention the expression vector capable of expressing the C/EBP protein may include a viral vector, e.g. a replication-incompetent retrovirus, an adenovirus, an adeno-associated virus or the like are included.

The expression vector may be introduced into host cells using methods known in the art. For example, the expression vector may be introduced into cells by transfection, microinjection, transduction, cell fusion, calcium phosphate precipitation, liposome-mediated transfection, DEAE-dextran-mediated transfection, polybrene-mediated transfection, electroporation, gene gun, and other known methods for introducing nucleic acid into cells (Wu et al., J. Biol. Chem., 267: 963-967, 1992).

The term used herein, "gene construct" means a functional unit necessary for the transfer or the expression of a gene of interest. The gene construct comprises apart from the gene of interest itself, a so-called promoter and a terminator which are required for expression. In most case, additional elements are included, e.g. marker genes which are also accompanied by a promoter and a terminator, other regulatory elements including enhancers and suppressors.

According to the transduced T cell precursor, the precursor T cells may be a CD4$^+$ cell, and the CD4$^+$ cell is a naïve T cell, a memory T cell, or an effector T cell. The naïve T cell may be a CD4$^+$CD25$^-$CD44$^-$ cell and the memory T cell may be a CD4$^+$ CD25$^-$CD44$^+$ cell.

In addition, in another aspect of the present invention, an induced regulatory T cell prepared by introducing a heterologous polynucleotide encoding C/EBP and overexpressing the C/EBP and capable of differentiating from the transduced T cell precursor thereby is provided.

The term "T cell" used herein means a lymphocyte involved in antigen-specific adaptive immune response and maturated in the thymus, and classified as naïve T cells which have never contacted antigens before, mature effector T cells which have met antigens and memory T cells may be included.

The term "effector T cell" used in this document refers to a cell which can differentiate into a variety of T cells capable of performing a specific immune response, a helper T cell, a cytotoxic T cell and a natural killer T cell are included.

As used herein, "T cell precursor" means a cell that can differentiate into a regulatory T cells induced by the overexpression of the C/EBP. For example, the above-described naïve T cell, a memory T cell, and an effector T cell are included.

The term "naïve T cell" used in this document means a mature T cell which has never contacted antigens before, or other thymus-derived cells containing cells with various phenotypes. Typically, CD62L$^{high}$CD44$^{low}$, CD45RA$^+$ CD62L$^+$, CD45RA$^+$CD27$^+$, CD45RA$^+$CCR7$^+$, and CD4$^+$ CD25$^-$CD44$^-$ cells among T cells are included.

As used herein, "memory T cell" is a cell which has potential to function as an effector T cell when a T cell that recognizes antigens is subjected to long-term survival after differentiation and selection process and then activated rapidly after the antigens re-invade an organism.

The term used herein, "cytotoxic T cell" means a cell expressing CD8 on the surface and, recognizing and removing target cells such as cells infected with retroviral vectors by binding to antigens associated with MHC class I molecules. The cytotoxic T cell is involved in graft rejection.

The term "helper T cell" used in this document, means a cell supporting other lymphocytes and expressing CD4 on the surface. The helper T cell supports the maturation of B cells into plasma cells or memory B cells and the activation of cytotoxic T cells and macrophages in the immune process. It includes $T_H1$, $T_H2$, $T_H3$, $T_H17$, $T_H9$, or Tfh subtypes.

The term "natural killer T cell" used in this document means a cell that recognizes glycolipid antigens displayed by a CD1d molecule and functions as an effector T cell and cytotoxic T cell.

The term "regulatory T cell" used herein means a cell that inhibits activity of abnormally activated immune cells and has immune regulatory function which plays important role in immune tolerance, and the regulatory T cell includes a natural regulatory T cell (nT$_{reg}$), an induced regulatory T cell (iT$_{reg}$) and a stabilized regulatory T cell. The natural regulatory T cell having an immuno-suppressive function is a CD4$^+$CD25$^+$ T cell expressing Foxp3 (foxhead box P3), and is produced in the thymus expressing IL-10 and presents in the frequency of 5 to 10% among peripheral CD4$^+$ T cells in a normal individual. The induced regulatory T cell which is a cell that also exhibits immuno-suppressive effect, expresses Foxp3 by self-stimulation or the stimulation of foreign antigens and differentiates in the periphery under a particular environment. It plays an important role in the immuno-suppression on the mucosal surface. The "stabilized regulatory T cell" used herein means a transduced regulatory T cell prepared by delivering C/EBP to nucleus of a regulatory T cell, or introducing a gene construct including a heterologous polynucleotide encoding the C/EBP to a regulatory T cell and overexpressing the C/EBP thereby.

The regulatory T cell, particularly the induced regulatory T cell is unstable and tends to dedifferentiate or transdifferentiate into other cell types by inhibitory cytokines such as INF-γ and IL-4. However, the regulatory T cell can be stabilized by introducing an exogenous C/EBP. Thus the stabilized regulatory T cell in accordance with an embodiment of the present invention overcomes the disadvantage, that is its instability by introducing the exogenous C/EBP.

The regulatory T cell according to one embodiment of the present invention may the natural regulatory T cell or the induced regulatory T cell. In The FoxP3 is a $T_{reg}$-specific transcription factor which controls most important features of T cells and can serve as a marker for assessing the purity of $T_{reg}$.

Since the induced regulatory T cell exhibits significantly improved stability after differentiation from the T cell precursor and the function of the induced regulatory T cell is maintained for a long time as described above, it may be useful for the treatment of immune disease.

The induced regulatory T cell in accordance with an embodiment of the present invention may be prepared by removing the inhibition of FoxP3 (forkhead box P3) expression by C/EBP expressed by heterologous polynucleotide encoding the C/EBP introduced into the T cell precursor, but not limited thereto. Herein, the differentiation of the naïve T cell into the induced regulatory T cell and the stabilization of the induced regulatory T cells by C/EBP or a heterologous polynucleotide encoding the C/EBP result from withdrawing the inhibition of Foxp3 expression due to inhibitory cytokines. The Foxp3 is a transcription factor that plays an important function in the differentiation of the regulatory T cell which differentiates in the thymus and periphery (Fontenot et al., *Nat. Immunol.* 4: 330-336, 2003; Chen, W. et al., *J. Exp. Med.* 198: 1875-1886, 2003). Although the differentiation of the T cell precursor into the induced regulatory T cell and the stabilization of the induced regulatory T cell by C/EBP protein may be accomplished by binding of C/EBP protein to methylated CpGs existing in TSDR of Foxp3 locus, relieving the inhibition of Foxp3 expression by inhibitory cytokines (e.g., IFN-γ and IL-4), and by inducing stable expression of Foxp3 thereby eventually, but not limited thereto.

The induced regulatory T cell may be prepared by introducing a heterologous polynucleotide encoding C/EBP into the T cell precursor and treating TGF-β to the T cell precursor.

The C/EBP used in accordance with an embodiment of the present invention may be various types of natural or synthetic C/EBP (CCAAT/enhancer binding protein) exhibiting the effect in accordance with an embodiment of the present invention, one of among α, β, δ, and ε isoforms. The β isoform was used in one embodiment according to the present invention.

Therefore, the transduced T cell precursor overexpressing C/EBP or the induced regulatory T cell differentiated therefrom may be useful for treating or preventing immune diseases and in this aspect of the present invention, a composition comprising one of more cells selected from the groups consisting of: a transduced T cell precursor prepared by introducing a gene construct comprising a polynucleotide encoding C/EBP (CCAAT/enhancer binding protein) to a T cell precursor and capable of differentiating into a regulatory T cell; an induced regulatory T cell differentiated from the transduced T cell precursor; and a stabilized regulatory T cell prepared by introducing a gene construct comprising a polynucleotide encoding C/EBP into a regulatory T cell and expressing the C/EBP thereby. The transduced T cell precursor, the induced regulatory T cell or the stabilized regulatory T cell may be Foxp3-positive.

The immune disease may be autoimmune disease or inflammatory disease or graft rejection.

As used herein, "autoimmune disease" is a disease caused by dysfunction of the immune system, and can be classified in various ways, for example as hypersensitive or hyporesponsive depending on reactive components involved in the immune system or responsiveness, or as innate or acquired. In one embodiment, the immune disease means a disease in which components consisting of mammalian immune system cause, mediate or contribute to a pathological condition in mammals. In addition, it may include diseases which are caused by hypersensitive immune response. Theses immune diseases may include immune deficiency syndrome, allergy, autoimmune disease, an inflammatory disease, and a graft rejection of cells, tissues or organs.

The term used herein "inflammatory disease" is a disease which is caused by inflammatory substances (inflammatory cytokines) secreted by immune cells such as macrophages, e.g., TNF-α (tumor necrosis factor-α), IL-1 (interleukin-1), IL-6, prostaglandin, leukotriene and nitric oxide (NO), and excessive exacerbation of human immune system due to harmful stimulations such as inflammatory agent and irradiation, etc.

On the other hand, it is necessary to overcome recipients' rejection of transplanted cells and organs for successful organ transplantation. As a major mediator of graft rejection is a T cell, the graft rejection is caused when a T cell receptor recognizes a major histocompatibility complex (MHC) expressed in a graft and an immune response is induced thereby. Therefore, in order to reduce the graft rejection, immunosuppressive agents are used and the common purpose of the immunosuppressive agents is to suppress T cell-mediated immune response against the graft, and the graft rejection may be treated by inhibiting the immune response using the regulatory T cell.

In the present invention, the autoimmune disease or inflammatory disease may be a biliary cirrhosis, chronic rheumatoid arthritis, insulin-dependent diabetes, ulcerative colitis, Crohn's disease, multiple sclerosis, autoimmune myocarditis, scleroderma, myasthenia gravis, multiple myositis/skin myositis, Hashimoto's disease, chronic Idiopathic thrombocytopenic purpura, cytopenia, Sjogren's syndrome, vasculitis syndrome and systemic lupus erythematosus but not limited thereto.

As used herein, the term "treatment" means, unless otherwise mentioned, reversing, alleviating, inhibiting progress or preventing or a disease or disorder or one or more symptoms of the disease or disorder, for example, arresting the progress of an immune disease, preventing spread of the immune disease, alleviating an autoimmune disease, prohibiting recurrence of the immune disease and/or relieving symptoms of the immune disease.

The composition in accordance with the present invention, as a pharmaceutical composition, may contain a therapeutically effective amount of C/EBP and/or a polynucleotide encoding the same as an active ingredient alone or one or more pharmaceutically acceptable carrier, excipient or diluent for ease of administration, absorption, storage of the active ingredient additionally.

Herein, the term "therapeutically effective amount" means an amount sufficient to prevent, improve or treat symptoms of autoimmune disease. The effective amount may be about 0.1~100 mg/day/kg of body weight, and particularly 0.5~10 mg/day/kg of body weight. However, the therapeutically effective amount may be adjusted depending on severity of the immune disease, age, body weight, health, sex, administration route and treatment period, appropriately. In addition, the composition for preventing or treating autoimmune diseases according to the present invention may be administered in combination with any known compounds having the therapeutic effect for preventing, improving or treating symptoms of the immune diseases. Those skilled in the art may determine suitable dosage using known information, for example Lieberman, Pharmaceutical Dosage Forms (Vols. 1-3, 1992); Lloyd, The Art, Science and Technology of Pharmaceutical Compounding (1999); Pickar, Dosage Calculations (1999); and Remington: The Science and Practice of Pharmacy, $20^{th}$ Edition, 2003, Gennaro, Ed., Lippincott, Williams & Wilkins.

Further, the term used herein "pharmaceutically acceptable" means that a substance is physiologically acceptable and does not cause allergic response or similar responses such as gastrointestinal disorder, and dizziness, etc. As the carrier, excipient, diluent, lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methyl hydroxybenzoate, propyl hydroxybenzoate, talc, magnesium stearate and mineral oil may be included. In addition, fillers, anti-coagulants, lubricants, wetting agents, fragrances, emulsifiers and preservatives may be included additionally.

In addition, the compositions of the invention may be formulated using methods known in the art to enable fast release, or sustained or delayed release of active ingredients when administered to a mammal. The formulation may include powders, granules, tablets, emulsion, syrup, aerosol, soft or hard gelatin capsule, sterile injectable solution, and sterile powder form.

The composition according to the present invention may be administrated by various routes, e.g., orally, parenterally, for example, suppositories, transdermal, intravenous, intraperitoneal, intramuscular, intralesional, intranasal, and intraspinal injection, and may also be administrated using an implantable device for the continuous or repeated release or sustained release. The composition may be administrated by dividing the number of administration times: once a day or several times within the desired range, but the administration period is not particularly limited.

The composition according to an embodiment of the present invention may be useful for treating and/or studying using induced regulatory T cells since it amplifies number of regulatory T cells by promoting the differentiation of induced regulatory T cells, as well as contributes to the stabilization of the induced regulatory T cells in order to maintain their functions and characteristics.

In another aspect of the present invention, a cell therapy agent for treating an immune disease comprising one or more cells selected from the groups consisting of: a transduced T cell precursor prepared by introducing a gene construct comprising a polynucleotide encoding C/EBP into a T cell precursor and capable of differentiating into a regulatory T cell; an induced regulatory T cell differentiated from the transduced T cell precursor; and a stabilized regulatory T cell prepared by introducing a gene construct comprising a polynucleotide encoding C/EBP to a regulatory T cell.

The term as used herein "cell therapy agent" means a therapeutic agent comprising autologous, allogenic or xenogenic cells prepared by proliferating, selecting in vitro and/or by modifying biological properties of the cells for the purpose of treating, diagnosing and preventing a certain disease. The cell therapy agent has been managed as a medicine in the United States since 1993, and in Korea since 2002.

In an embodiment, the cell therapy agent may be used for ex vivo cell therapy which means isolating a T cell precursor from a subject to be treated, treating the T cell precursor with C/EBP or introducing a heterologous polynucleotide encoding the C/EBP according to the present invention to the T cell precursor and differentiating the T cell precursor into an induced regulatory T cell thereby in vitro and transplanting the induced regulatory T cell to the subject.

The cell used for the cell therapy agent of the present invention may be an autologous, allogenic, or xenogenic cell, in particular an autologous cell.

The T cell precursor used in the cell therapy of the present invention includes a naïve T cell, memory T cell, effector T cell, $CD4^+$ T cell or $CD8^+$ T cell. The T cell precursor used in cell therapy according to the present invention may be isolated from monocytes in the peripheral blood and cultivated using known methods. For example Raulf-Heimsoth (*Methods Mol. Med.*, 138: 17-30, 2007) may be referred.

In addition, the T cell precursor may be isolated using flow cytometry, or known commercially available kits, for example, the isolation of naïve T cells and memory T cells from peripheral blood may be performed using an isolation kit of Miltenyi Biotec, Inc.

A medium as used in the process may be any general medium used for the cultivation and/or proliferation of T cells. Preferably, the medium is a medium containing serum (e.g., fetal calf serum, horse serum and human serum). The medium used in the present invention may be, for example, RPMI series, Eagle's MEM (Eagle's minimum essential medium, Eagle, H. *Science* 130: 432, 1959), α-MEM (Stanner, C. P. et al., *Nat. New Biol.* 230: 52, 1971), Iscove's MEM (Iscove, N. et al., *J. Exp. Med.* 147: 923, 1978), 199 medium (Morgan et al., *Proc. Soc. Exp. Bio. Med.*, 73: 1, 1950), CMRL 1066, RPMI 1640 (Moore et al., *J. Am. Med. Assoc.* 199: 519, 1967), F12 (Ham, *Proc. Natl. Acad. Sci. USA* 53: 288, 1965), F10 (Ham, R. G. *Exp. Cell Res.* 29: 515, 1963), DMEM (Dulbecco's modified Eagle's medium, Dulbecco, R. et al., *Virol.* 8: 396, 1959), mixture of DMEM and F12 (Barnes, D. et al., *Anal. Biochem.* 102: 255, 1980), Way-mouth's MB752/1 (Weymouth, C. J. *Natl. Cancer Inst.* 22: 1003, 1959), McCoy's 5A (McCoy, T. A. et al., *Proc. Soc. Exp. Biol. Med.* 100: 115, 1959) and MCDB series (Ham, R. G. et al., *In Vitro* 14: 11, 1978) but not limited thereto. In these media, the other components, e.g., antibiotics or antifungal agents (e.g., penicillin and streptomycin) and glutamine may be included.

The isolated cell used in the cell therapy agent according to the present invention may be separated and/or identified by flow cytometry. This flow cytometry is performed using a specific T cell surface marker. For example, the induced regulatory T cells can be confirmed by detecting markers, such as $CD4^+CD25^+CD127^{Low}$.

The cell therapy agent according to the present invention overexpresses C/EBP protein. The methods for overexpressing a protein in cells are well known in the art. A heterologous polynucleotide encoding the C/EBP may be introduced to a cell according to an embodiment of the present invention after constructing a recombinant expression vector by being cloned and operably linked to a promoter of an appropriate eukaryotic expression vector, for example, viral vector, retroviral vector or plasmid vector. The expression vector and methods for introducing the polynucleotide to cells may be referred as described above.

The route of administration of a pharmaceutical composition comprising the cell therapy agent or cells according to the present invention may be administrated via any general route as it can be delivered to a target tissue.

A parenteral administration, e.g., intraperitoneal administration, intravenous administration, intramuscular administration, subcutaneous administration, intrasynobial administration may be used but not limited thereto.

The therapeutic agent or composition may be formulated in an appropriate preparation along with general pharmaceutically acceptable carriers. The pharmaceutically acceptable carrier may be a carrier for parenteral administration, for example, water, a suitable oil, saline, aqueous glucose, and glycol, etc. and may further include stabilizers and preservatives. A suitable stabilizer may be sodium bisulfite, sodium sulfite or an antioxidant, such as ascorbic acid. A suitable preserving agent includes benzalkonium chloride, methyl- or propyl-paraben, and chlorobutanol. In addition, the cell therapy composition according to the present invention, if necessary according to administration method and formulation, may include suspending agent, solubilizing agent, stabilizer, isotonic agent, preservative, adsorption inhibitor, surfactant, diluent, excipient, pH adjuster, soothing agent, buffering agents, and appropriate antioxidant. The pharmaceutically acceptable carriers and the preparation suitable for the present invention, including those described above is described in detail in the literature [Remington's Pharmaceutical Sciences, latest edition].

The cell therapy agent according to an embodiment of the present invention may be prepared in a unit dosage form or filled in a multi-dose container by formulating with pharmaceutically acceptable carriers and/or excipients according to methods that can be easily performed by those skilled in the art. The term, "therapeutically effective amount" means an amount of active ingredient or pharmaceutical composition capable of inducing biological or medical response in a tissue system, in animal or human, which is thought by researchers, veterinarians, medical doctors and other clinical persons, and includes an amount that leads to relieving the disease or symptoms of the disorder. It is obvious in the art that the therapeutically effective amount of the cell therapy agent included in the composition of the present invention will be varied according to the desired effect.

Therefore, the optimal dose of the cell therapy agent may be readily determined by those skilled in the art, and may be adjusted according to various factor such as type of disease, severity of disease, the amount of other components contained in the composition, type of formulation, and patient's age, body weight, general health, sex and diet, period of administration, route of administration, excretion rate of the composition, treatment period, response sensitivity, and drugs administrated simultaneously. Those skilled in the art may adjust the dosage appropriately considering the above factors. The cell therapy agent according to an embodiment of the present invention may be administrated to a region (cell, tissue, or organ) which requires treatment of immune disease.

Considering all the above factors, it is important to include at least an amount that can achieve the maximum effect without side effects. For example, the dosage of the cell therapy agent may be $1.0 \times 10^5$ to $1.0 \times 10^8$ cells/kg of body weight, more preferably from $1.0 \times 10^6$ to $1.0 \times 10^8$ cells/kg of body weight based on the content of the induced regulatory T cells, an active ingredient. For the non-human animal, the same dose per kg of human, or for example, a converted dose using volume ratio (e.g., mean value) of organs between the subject animal and human may be administrated. The subject animal to be treated according to the present invention, may be a human, or other mammals, specifically including human, monkey, mouse, rat, rabbit, sheep, cattle, dog, horse, and pig, etc.

According to an embodiment of the present invention, the naïve T cell, the memory T cell and the effecter T cell may differentiates into an induced regulatory T cell by overexpressing C/EBP and the induced regulatory T cell may be stabilized and thus may be useful for treating or preventing the immune disease.

In another aspect of the present invention, the provided is a method of treating a subject suffering autoimmune disease: comprising administrating therapeutically effective amount of the transduced T cell precursor which is prepared by introducing a heterologous polynucleotide encoding C/EBP to a T cell precursor and capable of differentiating into an induced regulatory T cell thereby or the induced regulatory T cells differentiated therefrom to the subject.

In the above method, the administration may be performed by injecting or transplanting the cells to a pathological site. The injection may be intravenous injection, intramuscular injection, subcutaneous injection, intraperitoneal injection, etc. but not limited thereto.

In another aspect of the present invention, the provided is a method of differentiating a T cell precursor into an induced regulatory T cell comprising: delivering C/EBP to nucleus of the T cell precursor; or introducing an expression vector including a heterologous polynucleotide encoding C/EBP to the T cell precursor and overexpressing the C/EBP thereby.

The method of differentiation according to an embodiment of the present invention may be used for treating a subject suffering from an immune disease and the method and the cell differentiated by the method may be used as tools for various studies.

The type of cells, proteins, genes and vectors used in the method according to an embodiment of the present invention may be referred as described above.

In addition, in another aspect of the present invention, the provided is a method of stabilizing a regulatory T cell: comprising delivering C/EBP to nucleus of a regulatory T cell; or introducing an expression vector including a heterologous polynucleotide encoding the C/EBP to the regulatory T cell and overexpressing the C/EBP thereby.

As used herein, "stabilizing a regulatory T cell" refers to maintain functions and properties of a differentiated regulatory T cell and/or an isolated regulatory T cell. The functions and properties may be identified by surface markers and the regulatory T cell expresses Foxp3 described below specifically.

During the differentiation of the T cell precursor, the T cell precursor may differentiate into a $T_H17$ cell besides the regulatory T cell. Although the $T_H17$ cell is generated in the presence of TGF-$\beta$ like $T_{reg}$ cell. However, the $T_H17$ cell requires IL-6 along with TGF-$\beta$ and expresses IL-17 whereas the $T_{reg}$ cell does not require IL-6. The $T_H17$ cell is involved in the first line of the inflammatory response shown in immune diseases unlike the $T_{reg}$ cell and known to maximize the signal of the inflammatory response and accelerates the progression of the diseases thereby. Thus, the inhibition of the differentiation of $T_H17$ cell may be useful for treating autoimmune diseases.

In another aspect of the present invention, the provided is a method of inhibiting differentiation of a T cell precursor into a $T_H17$ cell comprising: comprising delivering C/EBP to nucleus of a T cell precursor; or introducing an expression vector including a heterologous polynucleotide encoding the C/EBP to the T cell precursor and overexpressing the C/EBP thereby.

The inhibiting according to an embodiment of the present invention may be accomplished by inhibiting binding ROR$\gamma$ to CNS2 (conserved noncoding sequence 2) of IL-17 region through the interaction between C/EBP and the ROR$\gamma$ as described in the example of the present invention, but not limited thereto.

The method may further comprise treating the T cell precursor to the regulatory T cell with TGF-$\beta$, in order to promote the differentiation of the T cell precursor or the stabilization of the regulatory T cell.

In those methods, the delivering C/EBP to nucleus of the T cell precursor or the regulatory T cell may be accomplished by various known methods described in prior arts such as US20110189159A1, WO2005120588A2, U.S. Pat. No. 8,859,507B2, US20030054007A1, EP0506884B1, US20030054007A1, and EP1676588A1, etc. In particular virus-like particles (US20110189159A1) fusion proteins comprising a G-protein coupled receptor binding sequence and a nuclear localization signal (WO2005120588A2), protein complex comprising an in vitro stabilization protein, a membrane translocation sequence domain, and an in vivo stabilization protein (U.S. Pat. No. 8,859,507B2), cationic lipids (US20030054007A1 and EP16766588A1 and a tat protein (EP0506884B1). Otherwise, just a means for delivering a protein into cytosol may be used instead of nuclear targeting signals because C/EBP itself has nuclear localization sequence (Williams, S. C. et al., Gene Expr., 6(6): 371-385, 997). The means or delivering a protein into cytosol may be various cell penetrating peptides (e.g., those described in U.S. Pat. No. 7,579,318B2; EP2090584A1: WO2014056813A1; U.S. Pat. No. 8,614,194B1; U.S. Pat. No. 8,044,019B2; WO2013098337A1, WO2014041505A1; Ma, L. et al., Mol. Pharm. 12(6): 2040-2048, 2015; Ruczynski, J. et al., Folia Histochem. Cytobiol. 52(4): 257-269, 2014: and Orzechowska, E. et at., BMC Cancer 14:771, 2014, etc.) but not limited thereto. The documents are incorporated herein by reference.

Hereinafter, examples are provided in order to facilitate understanding of the present invention. However the following examples do not limit the scope of the present invention but are provided to disclose the present invention completely and help those skilled in the art understand the technical features of the present invention.

EXAMPLES

The experimental methods employed in the examples are as follows.

Mouse: All mice were bred and maintained in specific pathogen-free barrier facilities at Seoul National University and were used according to protocols approved by the Institutional Animal Care and Use Committees (IACUC) of Seoul National University. C57BL/6 and Scurfy mice were purchased from The Jackson Laboratory. Foxp3$^{EGFP}$ mice were kindly provided by T. A. Chatila (University of California at Los Angeles).

Antibodies and Reagents: The mAbs against CD3$\epsilon$ (2C11), CD28 (37.51), PE-conjugated IL-17A (TC11-

18H10), PE-conjugated CD-25 (PC61) and biotin-conjugated human CD271 were purchased from BD Pharmingen; PE-Cy7-conjugated CD4 (GK1.5), APC-conjugated Foxp3 (FJK-16s), APC-eFluor780-conjugated CD45.1 (A20), biotin-conjugated CD44 (IM7), FITC-conjugated CD44 (IM7), IL-4 (11B11) and IFN-γ (XMG1.2) from eBiosciences, Inc.; TGF-β1,2,3 (1D11) from R&D Systems, Inc.; C/EBPβ (C-19), RORγ (H-190) from Santa Cruz Biotechnology, Inc. Recombinant human TGF-β1 was purchased from eBiosciences, Inc. IL-6, IFN-γ, IL-4 was purchased from Peprotech, Inc. and all-trans retinoic acid and 5-azacytidine from Sigma, Inc.

In vitro T cell differentiation: All cultures for T cells used RPMI-1640 medium supplemented with 10% FBS, 2 mM glutamine, supplemented with 10% FBS, 100 U/ml penicillin, 100 μg/ml streptomycin and 55 μM 2-mercaptoethanol. CD4+ T cells were activated with plate-bound anti-CD3 (3 μg/ml) and soluble anti-CD28 (0.5 μg/ml) antibodies with cytokines and antibodies as noted in figure legends. Concentrations used are as follows; 0.5 ng/ml TGF-β, 10 U/ml IL-2, 10 ng/ml IFN-γ, 1 ng/ml IL-4, 20 ng/ml IL-6, 5 μg/ml anti-IFN-γ, 5 μg/ml anti-IL-4, 10 ng/ml anti-TGF-β, 1 μM 5-aza, 100 nM ATRA. For analysis of IL-17A expression, re-stimulation was carried out by addition of phorbol 12-myristate 13-acetate (PMA, 10 ng/ml, Sigma-Aldrich, Inc.), ionomycin (0.5 μg/ml, Sigma-Aldrich, Inc.) and Brefeldin A (eBiosciences, Inc.) for additional 3 hr. Memory supernatant was harvested after 48 hr from cultures of memory CD4+ T cells activated with plate-bound anti-CD3 (3 μg/ml) and anti-CD28 (3 μg/ml) antibodies.

Retroviral transduction: Naïve CD4+ T cells were stimulated for 24 hr with plate-bound anti-CD3 (3 μg/ml) and soluble anti-CD28 (1 μg/ml) antibodies together with soluble anti-IFN-γ (5 μg/ml), anti-IL-4 (5 μg/ml) and anti-TGF-β (10 ng/ml) antibodies, and spin-infected for 1 hr with retroviral supernatant containing 6 μg/ml polybrene from Phoenix packaging cells transfected with retroviral expression plasmids. After 20 hr incubation with anti-IFN-γ, anti-IL-4 and anti-TGF-β antibodies at 37° C., viral supernatants were replaced with T cell culture medium containing the appropriate cytokines and antibodies.

Immunocytochemistry: For analysis of Foxp3 and IL-17A expressions, CD4+ T cells were fixed after staining with anti-CD4-PE-cy7 mAb, and then permeablized with cytofix/permeabilization solution (BD Pharmingen, Inc.). The cells were stained with anti-Foxp3-APC and anti-IL-17A-PE mAbs and then analyzed using FACS Canto II (BD Biosciences, Inc.) according to the manufacturer's instruction.

DNA construct: Full-length mouse C/EBPα, β, and δ cDNAs were amplified from the genome DNA. C/EBPε, ζ and RORγt cDNAs were amplified by RT-PCR using total RNA of mouse bone marrow cells, TH17 cells generated in vitro, respectively. The amplified products were sequenced and inserted into retroviral vectors MCSV-IRES-GFP (MigR1, Pear et al, *Blood*, 92 (10): 3780-3792, 1998) and MSCV-IRES-hNGFR (MIN, Izon et al., *Immunity*, 14: 253-264, 2001) and pcDNA3 (Invitrogen, Inc.). The MigR1 and MIN vectors were kindly provided by W. S. Pear (University of Pennsylvania). The two retroviral vectors are available at Addgene, Inc. (USA). Dominant-negative C/EBP (AC/EBP) was kindly provided by C. Vinson (National Institutes of Health) and inserted into MigRI vector. IL-17A promoter and IL-17 CNS2 region were amplified from mouse genomic DNA by PCR and cloned into XhoI/HindIII and NheI/XhoI sites of pGL3-Basic vector (Promega, Inc.).

Cell sorting: Peripheral CD4+ T cells were obtained from spleen and lymph node cells of 8- to 12-week-old C57BL/6 mice. Naïve CD4+ T cells (CD4+CD25−CD44−) and memory CD4+ T cells (CD4+CD25−CD44+) were isolated using the FACS Ariall (BD Biosciences, Inc.). Foxp3$^{EGFP}$-reporter mice-derived naïve CD4+ T cells (CD4+CD44− Foxp3−) were also isolated using the FACS Ariall. The purity of naïve and memory CD4+ T cells was consistently higher than 98% and 95%, respectively.

Bone marrow transplantation for obtaining naïve CD4+ Foxp3$^{sf}$ T cells: T cell-depleted bone marrow cells isolated from CD45.2+Foxp3$^{sf}$ mice were mixed with bone marrow cells of B6.SJL mice (CD45.1+) at a 1:1 ratio. The mixed bone marrow was then injected intravenously into B6.SJL mice, which received 500 rad γ-irradiation 1 day before the transplantation.

Quantitative real-time RT-PCR: Total RNA from CD4+ T cells was prepared with TRIzol (Invitrogen, Inc.) and treated with DNase I (Invitrogen, Inc.) according to the manufacturer's instructions. cDNA was synthesized with SuperScript III (Invitrogen). Quantitative real-time PCR was performed on ABI StepOnePlus real-time PCR system using SYBR green PCR master mix (Applied Biosystems).

Primer sets used are as follows:

```
C/EBPβ forward,
                                    (SEQ. ID. NO.: 1)
5'-AGCGGCTGCAGAAGAAGGT-3';

C/EBPβ reverse,
                                    (SEQ. ID. NO.: 2)
5'-GGCAGCTGCTTGAACAAGTTC-3';

Foxp3 forward,
                                    (SEQ. ID. NO.: 3)
5'-GGACAGACCACACTTCATGCA-3';

Foxp3 reverse,
                                    (SEQ. ID. NO.: 4)
5'-GCTGATCATGGCTGGGTTGT-3';

β-actin forward,
                                    (SEQ. ID. NO.: 5)
5'-CAACGAGCGGTTCCGATG-3';
and β-actin reverse,
                                    (SEQ. ID. NO.: 6)
5'-GCCACAGGATTCCATACCCA-3'.
```

Chromatin immunoprecipitation analysis: ChIP analysis was performed according to the manufacturer's guide (Upstate/Millopore). In brief, cells (2-3×10$^6$) were fixed with 1% formaldehyde, followed by sonication. Sonicated cell supernatant was precleared by incubation with Protein A/salmon sperm DNA (Upstate/Millipore) and then was immunoprecipitated overnight with antibodies (normal rabbit IgG, Millipore; anti-C/EBPβ, Santa Cruz Biotechnology, Inc.) followed by incubation with protein A/salmon sperm DNA for 1 hr. Precipitates were defixed and DNA was purified. Precipitated DNA was subjected to real-time PCR. The PCR primer set used is as follows:

```
Foxp3 TDSR forward,
                                    (SEQ. ID. NO.: 7)
5'-CCTCCTTGTTGCCGATGAA-3';
and Foxp3 TDSR reverse,
                                    (SEQ. ID. NO.: 8)
5'-CACAACCTGAACTTGGCCAGAT-3'.
```

Bisulfite sequencing: Genomic DNA was purified from purified CD4+ T cells from male mice using LaboPass™ tissue Mini Kit (Cosmo Genetech, Inc.). Methylation analysis was performed using Methyl Detector kit (Active Motif, Inc.) according to manufacturer's protocols. PCRs were performed using PfuTurbo Cx hotstart DNA polymerase (Stratagene, Inc.) with the primer set (Foxp3 TDSR forward, 5'-TTTTGGGTTTTTTTGGTATTTAAGA-3', SEQ. ID. NO.: 9; and Foxp3 TDSR reverse, 5'-TTAAC-CAAATTTTTCTACCATTAAC-3', SEQ. ID. NO.: 10). PCR products were cloned into pGEM-T easy vector (Promega, Inc.). Recombinant plasmids from the individual bacterial colonies were purified and sequenced.

Experimental colitis animal model: RAG-2$^{-/-}$ mice were injected with intravenously with CD4$^+$CD45RB$^{high}$ cells (5×10$^5$) alone or together with FACS-sorted CD4$^+$GFP$^+$ cells (2×10$^5$) infected with control retroviral vector (MigR1) or C/EBPβ-encoding retroviral vector and cultured for 2 days in memory supernatant supplemented with TGF-β. Mice were observed daily and weighed weekly. Eight weeks after cell transfer the mice were sacrificed for histological analysis. Tissue samples from distal portion of the large intestine were prepared and fixed in 10% formalin. Fixed tissues were embedded in paraffin, and were cut into 6 μm sections and stained with hematoxylin and eosin.

Cell line: Jurkat cell line was cultured in RPMI 1640 medium supplementary with 10% FBS, 100 U/ml penicillin, 100 μg/ml streptomycin and 55 μM 2-mercaptoethanol.

Nuclear extraction and immunoblotting: Nuclear extracts were prepared as described previously (Ko, M. et al., *J. Biol. Chem.* 279: 21916-21923, 2004). Protein samples were solubilized in loading buffer, subjected to SDS-PAGE (10-12.5% gels) and transferred to an Immunobilon-P membrane (Millipore, Inc.). Membranes were hybridized with anti-C/EBPβ antibody, and then visualized using an ECL system (Pierce, Inc.).

Immunoprecipitation: 293T cells were transiently transfected as indicated in the figure legends. The cells were lysed in RIPA buffer (50 mM Tris-HCl (pH 8.0), 150 mM NaCl, 0.1% SDS, 0.5% deoxycholate, and 1% Triton X-100) supplemented with protease inhibitors. The supernatants were precleared once with protein G-Sepharose 4 fast flow (GE Healthcare) in RIPA buffer. Anti-Myc antibody was incubated with the supernatant for 4 hr at 4° C., and then with protein G-Sepharose for 1.5 hr. Bound antibody/antigen complexes were washed 3 times in RIPA buffer. Washed immune complexes were subjected to immunoblotting.

Electrophoretic mobility shift assay (EMSA): Double-stranded oligonucleotides were end-labeled with [γ-$^{32}$P]ATP by using T4 polynucleotide kinase followed by purification over a MicroSpin™ G-25 column (Amersham Biosciences). The DNA binding reaction was performed at room temperature for 15 min in a total volume of 20 μl containing nuclear extracts (3 μg), end-labeled probe, and 2 μg of poly(dl-dC) in binding buffer containing 10 mM HEPES (pH 7.9), 80 mM KCl, 0.05 mM EDTA, 1 mM MgCl$_2$, 1 mM dithiothreitol, and 6% glycerol. In some experiments, antibodies for supershifting (1 μl) were added to the reaction. The DNA-protein complex was resolved in a nondenaturing 5% polyacrylamide gel in 0.5×TBE buffer. Gels were dried and exposed for autoradiography.

The following oligonucleotide were synthesized and used as a probe:

```
Foxp3 TSDR methyl-CRE forward,
                          (SEQ. ID. NO.: 11);
5'-CCGGCCGCCATGAᵐCGTCAATGGCAGAAA-3';

Foxp3 TSDR methyl-CRE reverse,
                          (SEQ. ID. NO.: 12)
5'-TTTCTGCCATTGAᵐCGTCATGGCGGCCGG-3';

Foxp3 TSDR unmethyl-CRE forward,
                          (SEQ. ID. NO.: 13)
5'-CCGGCCGCCATGACGTCAATGGCAGAAA-3';

Foxp3 TSDR unmethyl-CRE reverse,
                          (SEQ. ID. NO.: 14)
5'-TTTCTGCCATTGACGTCATGGCGGCCGG-3';

ROR element (RORE) in IL17 CNS2 forward,
                          (SEQ. ID. NO.: 15)
5'-GAAAGTT TTCTGACCCACTTTAAATCAATTT-3';

ROR element (RORE) in IL17 CNS2 reverse,
                          (SEQ. ID. NO.:16)
5'-AAATTGATTTAAAGTGGGTCAGAAAACTTTC-3'.
```

Underlines of the sequences represent CRE sites.

Luciferase assay: Luciferase assay was performed in Jurkat cells. Transfection was performed using the Gene Pulser-II electroporator (Bio-Rad, Inc.). The luciferase activity was assayed according to the manufacturer's protocol (Promega, Inc.). RSV-LacZ plasmid was co-transfected, and β-galactosidase activity was measured to normalize the transfection efficiency.

Statistical Analysis: Two-tailed unpaired t-tests were performed using Prism software. P values less than 0.05 were considered significant, and the level of significance was indicated as *P<0.05, P<0.01 and *P<0.001.

Example 1: C/EBPβ Expression Upregulation by RA

The present inventors investigated the effect of retinoic acid (RA) on the expression of C/EBPβ in näive CD4+ T cells during the TGFβ-induced Foxp3$^+$ T$_{reg}$ differentiation. As a result, it was found that the expression of C/EBPβ in näive CD4$^+$ T cells during the TGFβ-induced Foxp3$^+$ T$_{reg}$ differentiation was increased by RA.

Figure 1B:
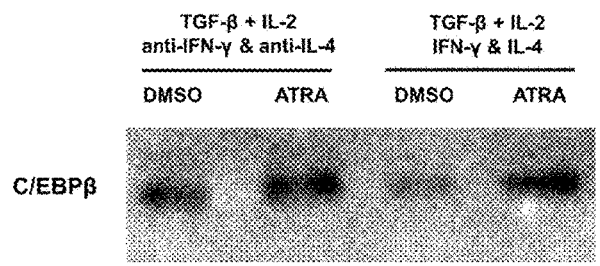

Purified CD4$^+$CD25$^-$CD44$^-$ näive T cells from C57BL/6 mice were cultured in iT$_{reg}$-polarizing conditions in vitro for 24 hr in the presence or absence of ATRA (all-trans retinoic acid) with or without inhibitory cytokines, IFN-γ and IL-4. Treatment of TGF-β plus retinoic acid enhanced the expression of C/EBPβ compared with stimulation with TGF-β alone at both mRNA and protein level (FIGS. 1A and 1B). The absence of the IFN-γ and IL-4 was accomplished by treatment of anti-IFN-γ and anti-IL-4 antibodies. However addition of exogenous IFN-γ and IL-4 made little difference in the expression of C/EBPβ.

Figure 1C:
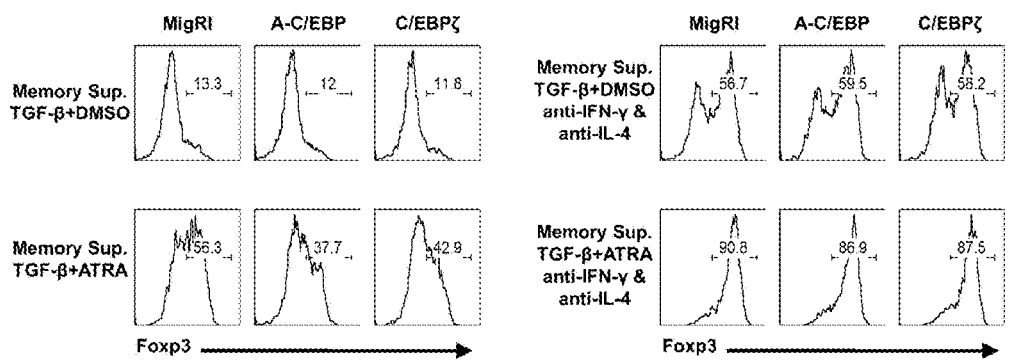
Figure 1D:
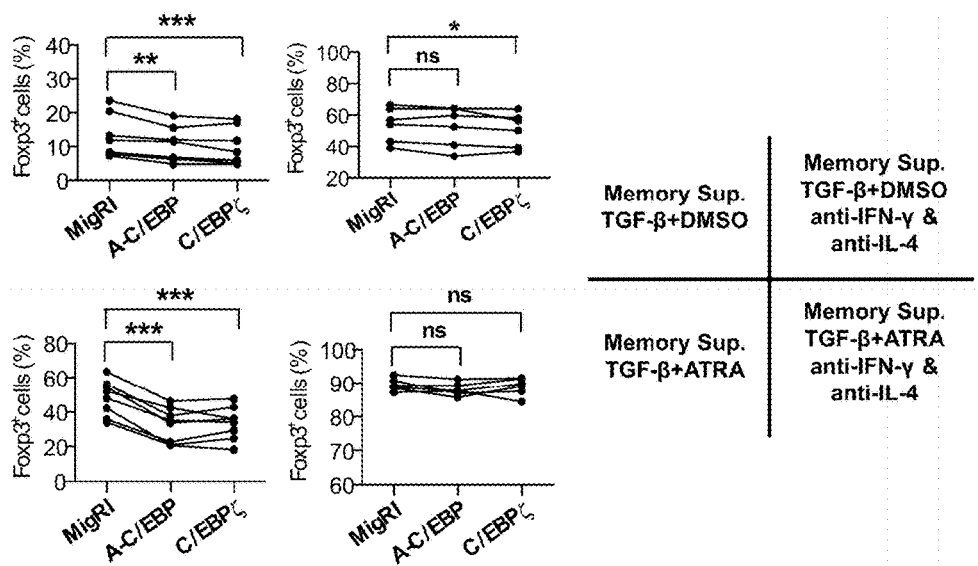
Figure 1E:
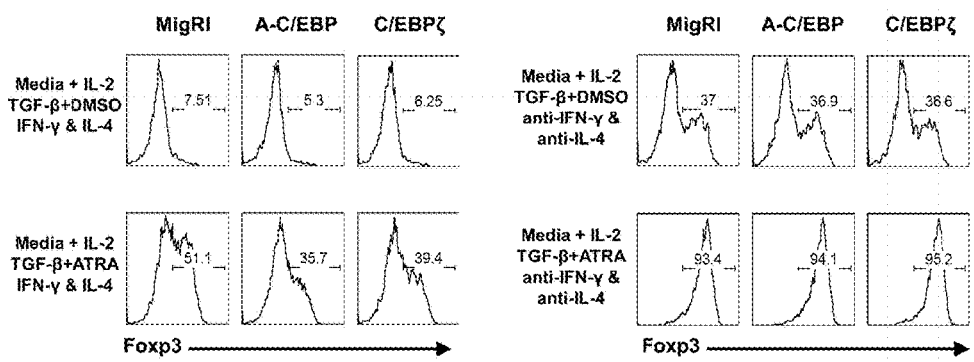
Figure 1F:
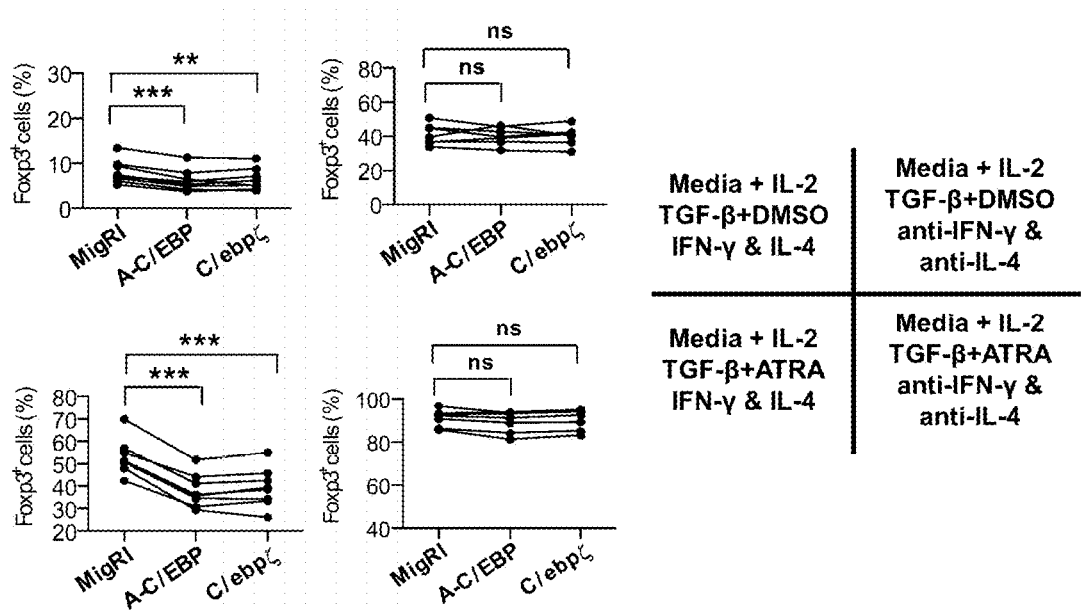

Example 2: C/EBP Acting in the Presence of an Inhibitory Cytokine in the Downstream of RA The present inventors investigated the function of C/EBP in iT$_{reg}$ differentiation by expressing dominant-negative C/EBP (A-C/EBP) or C/EBPζ in näive CD4$^+$ T cells using a retroviral vector and culturing them under iT$_{reg}$-polarizing conditions in the presence of culture supernatant derived from CD4$^+$CD25$^-$CD44$^+$memory T cells stimulated with anti-CD3 and anti-CD28 antibodies (hereinafter, referred to as "memory supernatant") with or without ATRA. Particularly iT$_{reg}$ differentiation was induced by adding same quantity of the memory supernatant to cell culture medium of cells transfected with C/EBP gene. The memory supernatant inhibits the induction of Foxp3 expression because it contains IFN-γ and IL-4 which are inhibitory cytokines. A-C/EBP specifically inhibits the DNA binding of the C/EBP family members (Chatterjee, R. et al. *J. Mol. Endocrinol.* 46: 175-192, 2011), and C/EBPζ is also a dominant-negative inhibitor of C/EBP (Ron, D. and Habener, J. F., Genes Dev. 6: 439-453, 1992). Enforced expression of A-C/EBP or C/EBPζ marginally reduced iT$_{reg}$ differentiation in the presence of the memory supernatant. However, addition of ATRA in the memory supernatant resulted in the significant reduction in iT$_{reg}$ differentiation of A-C/EBP or C/EBP-transduced cells compared with control vector-transduced cells (left panel of FIGS. 1C and 1D). On the other hand, in the presence of neutralizing antibodies against IFN-γ and IL-4, the effect of ATRA was abolished, and the down-regulation of Foxp3 expression by ectopic expression of A-C/EBP or C/EBPζ in the presence of memory supernatant was not observed (right panel of FIGS. 1C and 1D). This result suggests that C/EBP functions mainly in the presence of inhibitory cytokines, IFN-γ and IL-4, and ATRA during iT$_{reg}$ differentiation. The function of C/EBP in the iT$_{reg}$ differentiation was also confirmed when memory supernatant was replaced with fresh media containing exogenous IFN-γ, IL-4, and IL-2 (FIGS. 1E and 1F). However this effect was now shown in the GFP-negative cells, suggesting that this is an inherent regulation within a cell.

Example 3: Complete Resistance Against Inhibitory Cytokines in iT$_{reg}$ Generation Process by C/EBPβ

Figure 2A:
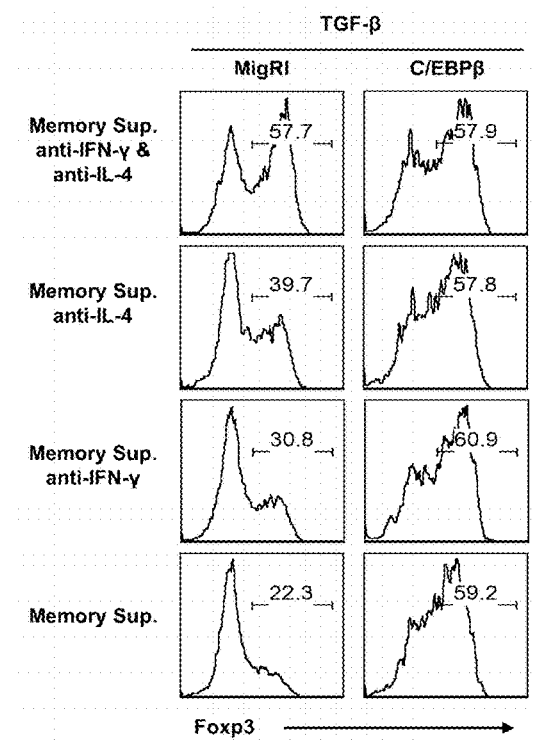
FIGS. 2A-2F represent that C/EBPβ can protect completely the inhibition of iTreg formation by IFN-γ and IL-4.
Figure 2B:
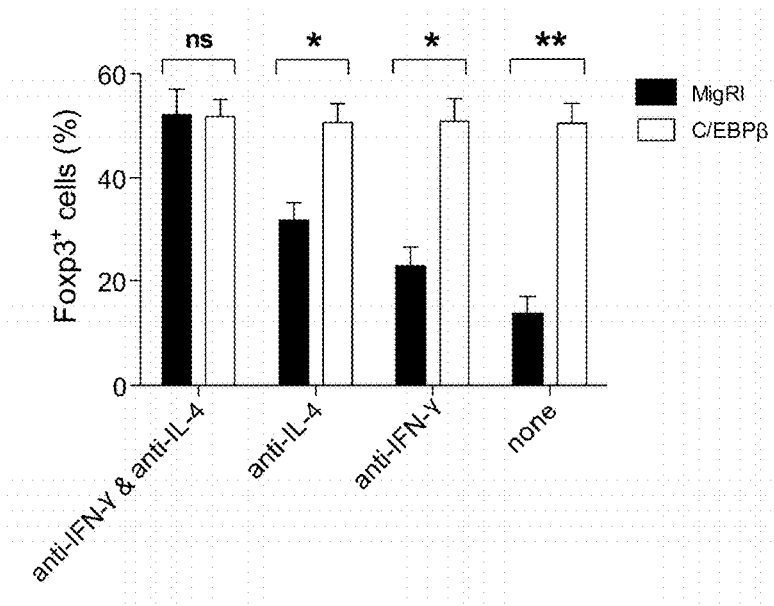
Figure 2C:
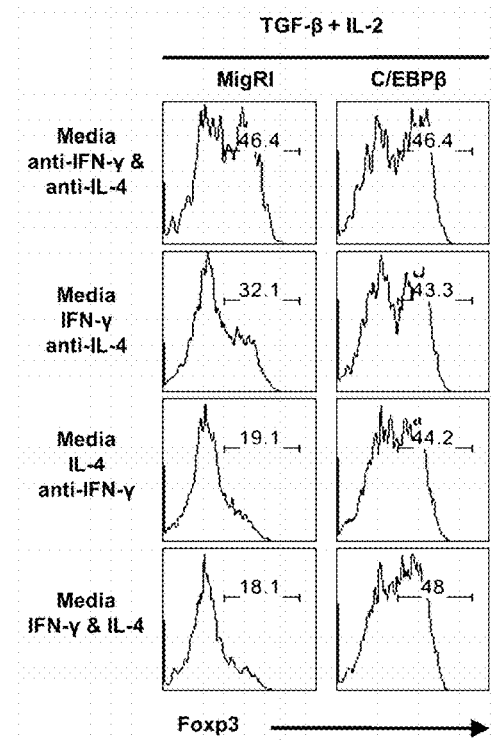
Figure 2D:
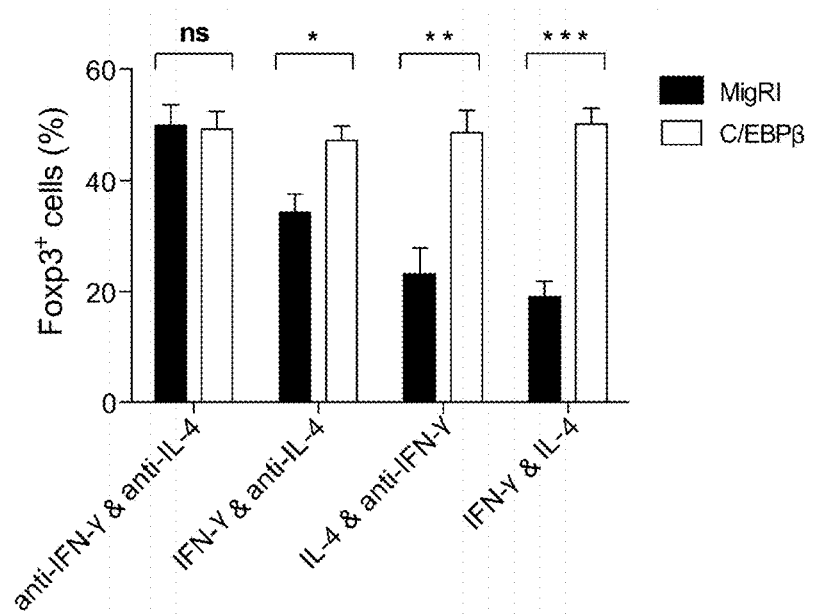
Figure 2E:
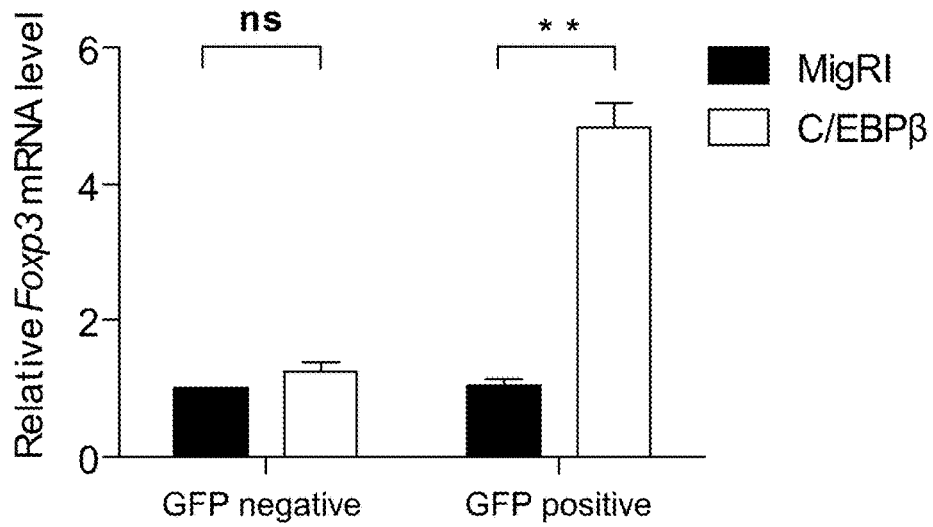

The present inventors investigated the effect of C/EBPβ expression in the iT$_{reg}$ differentiation, reasoning that its enforced expression should attenuate the effect of inhibitory cytokines on iT$_{reg}$ generation. Ectopic expression of C/EBPβ resulted in complete resistance to Foxp3 suppression by memory supernatant (FIGS. 2A and 2B). This effect was observed as long as IFN-γ, IL-4, or both of them are present in memory supernatant, which was also confirmed by addition of exogenous inhibitory cytokines (FIGS. 2C and 2D). The increased expression of Foxp3 in C/EBPβ-transduced cells was again confirmed by qPCR using GFP$^+$ cells from the culture containing memory supernatant (FIG. 2E).

These results indicate that C/EBPβ upregulates Foxp3 expression at the mRNA level. As C/EBP isoforms regulate several physiological events in a redundant manner, the present inventors compared the ability of the four family members, C/EBPα, β, δ, and ε, to regulate Foxp3 expression. As a result, C/EBPα gave resistance against inhibitory cytokines like C/EBPβ, but C/EBPδ and C/EBPε showed less effect than C/EBPβ (FIGS. 7A and 7B).

Figure 2F:
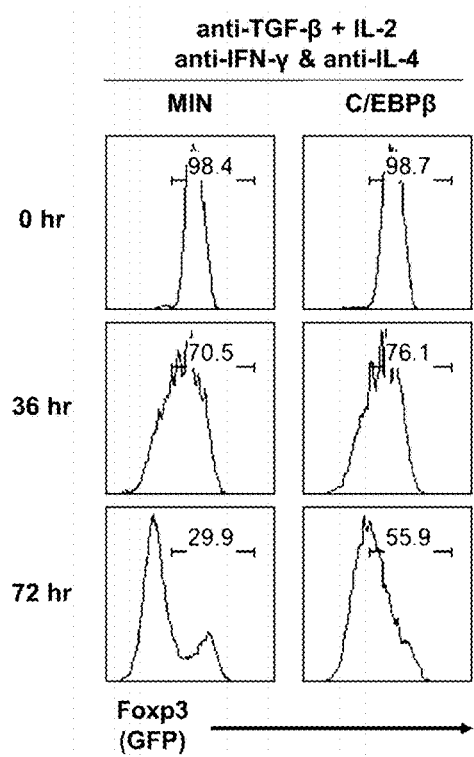

TGF-β-induced Foxp3$^+$ iT$_{reg}$ cells rapidly lost their Foxp3 expression upon restimulation in the absence of TGF-β (Polansky, J. K. et al., *Eur. J. Immunol.* 38: 1654-1663, 2008). However, it was found that ectopic expression of C/EBPβ greatly retarded the loss of Foxp3 (FIG. 2F).

Figure 3A:
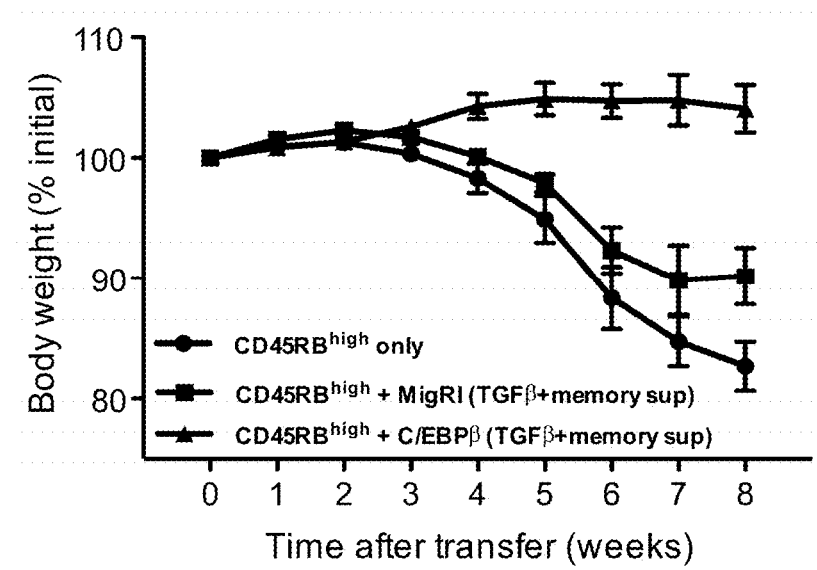
FIGS. 3A-3C represent effect of iTreg cells infected with retroviral vector comprising a polynucleotide encoding C/EBPβ on the suppression of colitis.
Figure 3B:
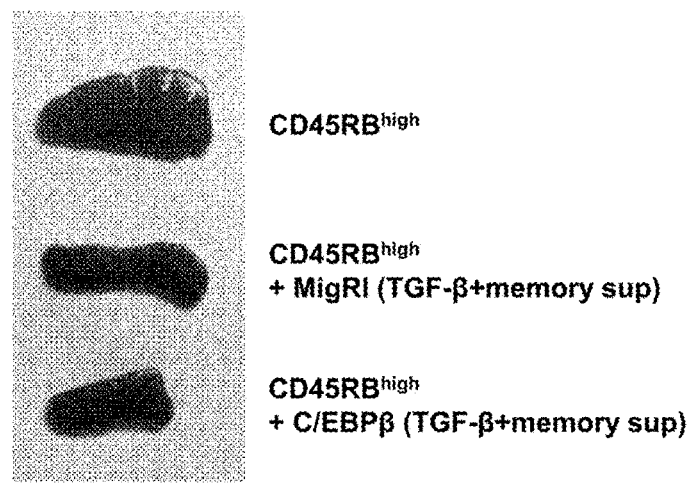
Figure 3C:
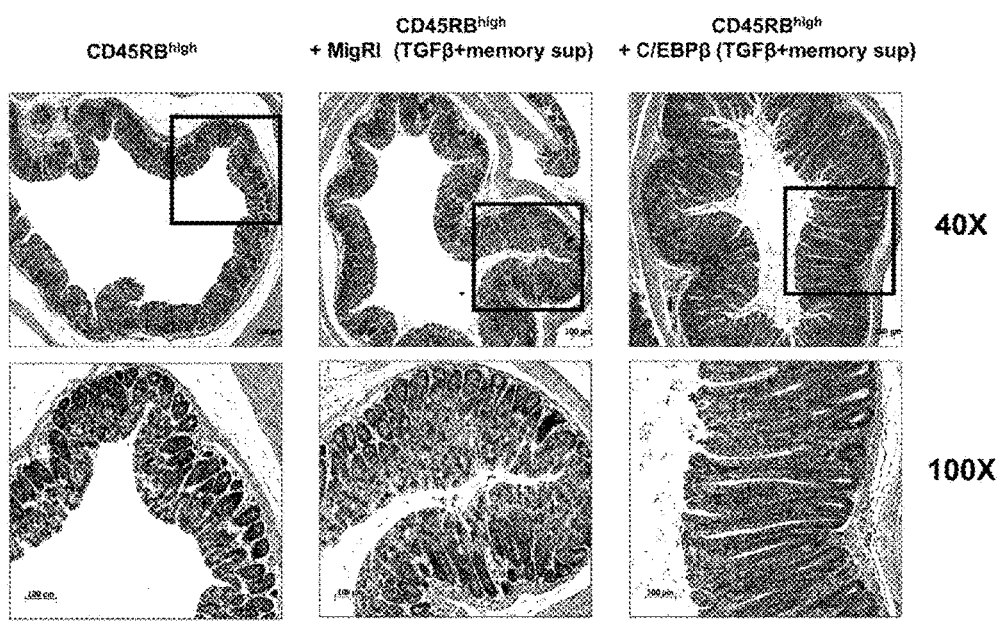

Example 4: Prevention of Colitis in Animal Model by C/EBPβ-Trasnsfected iTreg Cells The present inventors analyzed in vivo suppressor capacity of Foxp3$^+$CD4$^+$ T cells exhibiting resistance to the inhibitory cytokines by enforcing expression of C/EBPβ. For this, an adoptive-transfer experiment using CD45RB$^{high}$CD4$^+$ T cells that induce colitis in immune-deficient mice (Polansky, J. K. et al. *Eur. J. Immunol.* 38: 1654-1663, 2008). Mice that received CD45RB$^{high}$CD4$^+$ T cells alone developed a wasting disease defined by progressive weight loss (FIG. 3A), splenomegaly (FIG. 3B) and severe colitis (FIG. 3C). Mice co-transferred with control vector-transduced CD4$^+$ T cells cultured in the presence of TGF-β and memory supernatant were slightly protected from the disease. In contrast, mice co-transferred with C/EBPβ-transduced CD4$^+$ T cells cultured in the same conditions did show significant relief from the disease, suggesting considerable attenuation of the pathogenic activity of CD45RB$^{high}$CD4$^+$ T cells.

Taken together, the above results suggest that C/EBP is not responsible for de novo generation of Foxp3$^+$ iT$_{reg}$ cells, but rather, confers resistance to the suppressive effect of inhibitory cytokines on Foxp3$^+$ iT$_{reg}$ differentiation, especially in the downstream of ATRA, and thereby ensures stable induction of Foxp3.

Figure 4A:
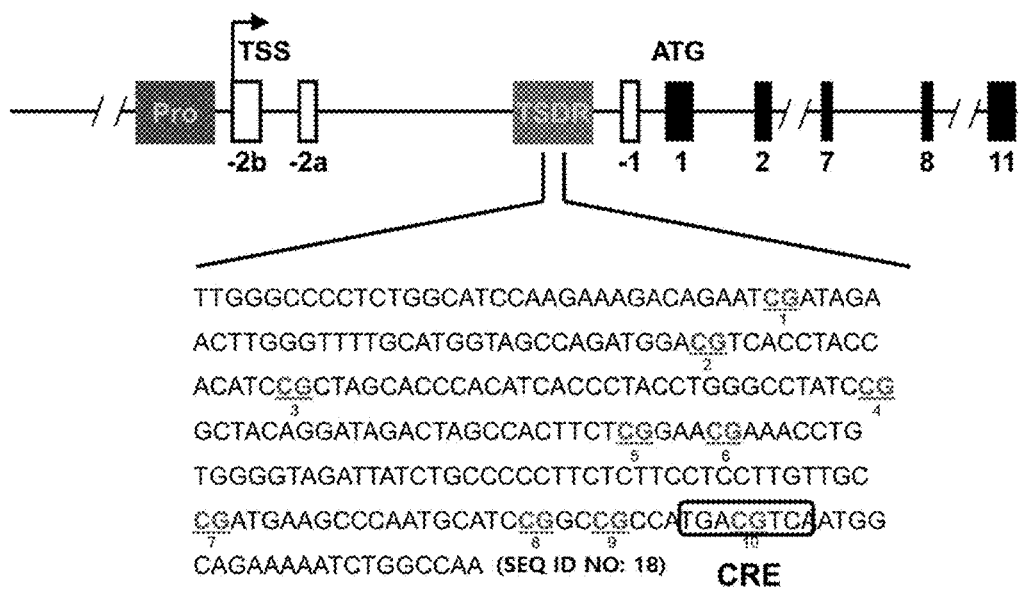
FIGS. 4A-4F represent that C/EBPβ binds to methylated CRE sequence of Foxp3 TSDR and acts in a methylation-dependent manner.
Figure 4B:
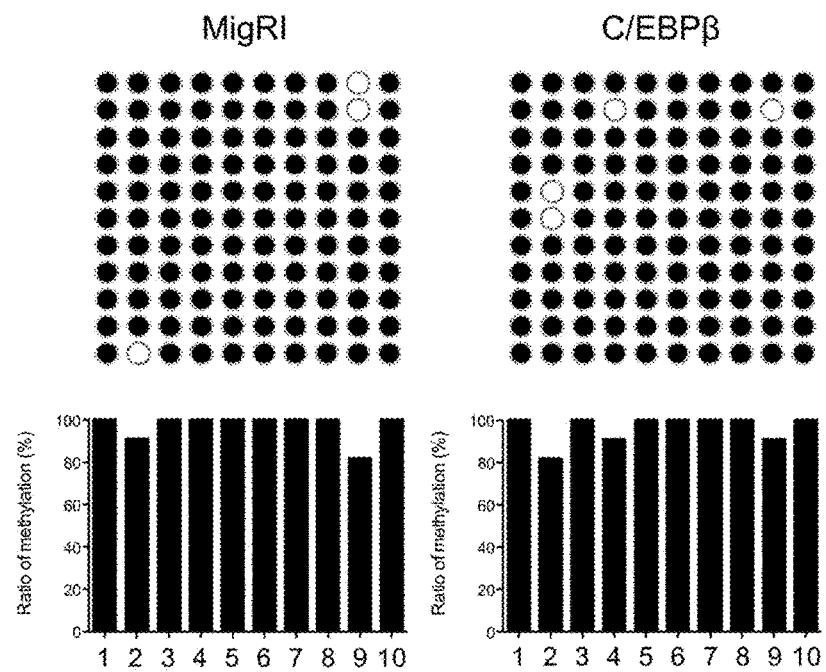
Figure 4C:
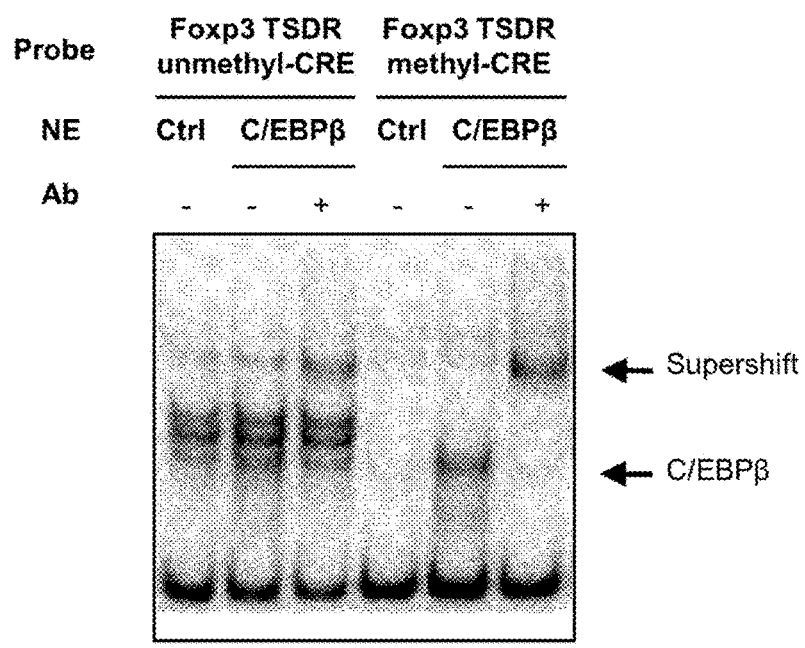
Figure 4D:
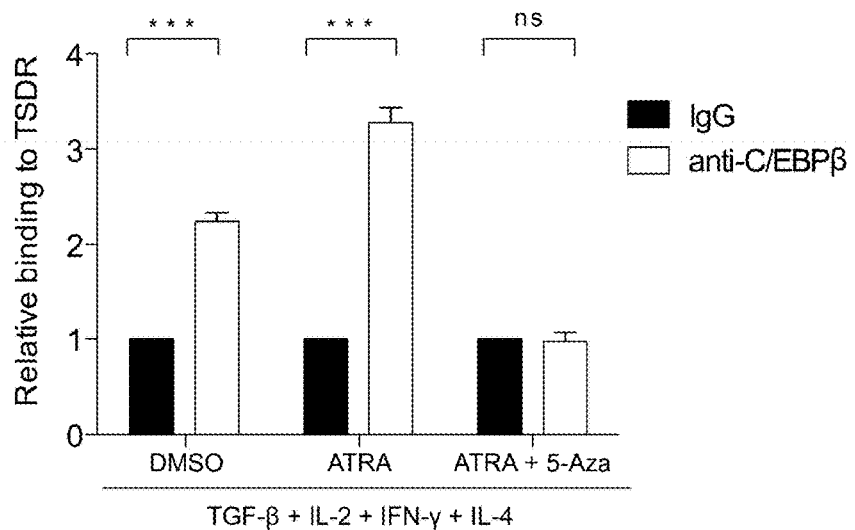
Figure 4E:
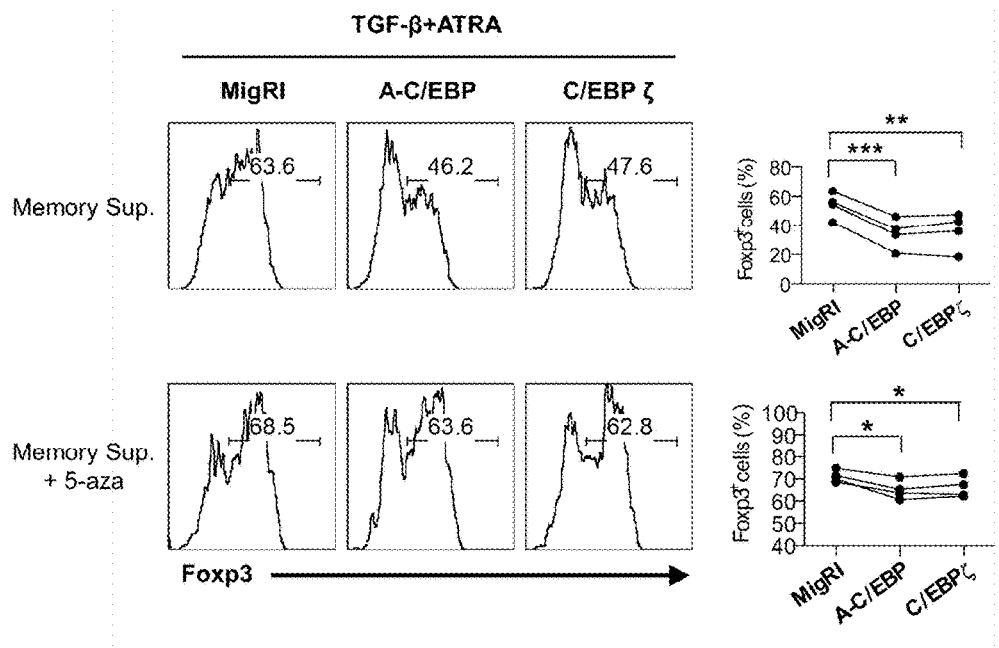
Figure 4F:
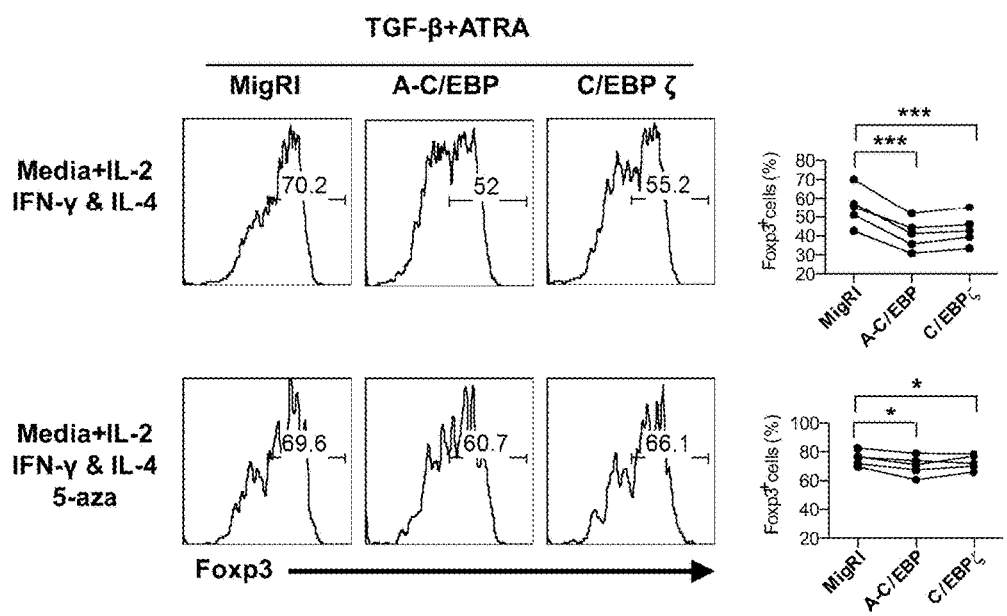

Example 5: Methylation-Dependent Activity Due to Binding of C/EBPβ to Methyl-CRE in Foxp3 TSDR The present inventors investigated the molecular mechanism by which C/EBP confers resistance to inhibitory cytokines during the TGF-β-induced generation of Foxp3$^+$ T$_{reg}$ cells. Recently, it has been shown that the DNA methylation status of the T$_{reg}$-specific demethylated region (TSDR) in the Foxp3 locus is critical for maintenance of Foxp3 (Floess, S. et al., *PLoS Biology* 5: e38, 2007; Polansky, J. K. et al., Eur. J. of immunology 38, 1654-1663, 2008; Huehn, J. et al., *Nat. Rev. Immunol.* 9: 83-89, 2009; Zheng, Y. et al., *Nature* 463: 808-812, 2010). The Foxp3 TSDR is more widely demethylated in nT$_{reg}$ cells than in iT$_{reg}$ cells, and iT$_{reg}$ cells are less stable than nT$_{reg}$ cells. However, bisulfite sequencing showed that ectopic expression of C/EBPβ did not affect the methylation status of the Foxp3 TSDR region (FIGS. 4A and 4B). CREB has been reported to act downstream of TCR signaling and bind to the Foxp3 TSDR CpG islands when this region is demethylated (Kim, H. P. et al., *J. Exp. Med.* 204: 1543-1551, 2007). It was shown that CpG methylation of the CRE sequence (TGA$^m$CGTCA, SEQ. ID. NO.: 17) creates C/EBP binding site. The present inventors performed electrophoretic mobility shift assay (EMSA) to examine the DNA binding activity of C/EBPβ to methyl-CRE sequence of the Foxp3 TSDR (FIG. 4C). As a result, Jurkat cells transfected with C/EBPβ displayed robust DNA binding activity to methyl-CRE sequence, which was completely shifted following addition of anti-C/EBPβ antibodies. A ChIP analysis on C/EBPβ binding also revealed that the binding site in the TGFβ-stimulated CD4$^+$ T cells was TSDR (FIG. 4D). In addition, the binding of C/EBPβ to TSDR was increased in the CD4$^+$ T cells stimulated with TGFβ and ATRA. The binding of C/EBPβ to TSDR was disappeared when CpG dinucleotides of genome DNA were demethylated by using 5-azacytidine (5-aza) whose methylation is impossible. This indicates that the methylation in the CRE promotes selective binding of C/EBPβ to the TSDR and the DNA methylation plays important role in the resistance against inhibitory cytokines which is induced by C/EBPβ. Particularly, addition of 5-aza in the memory supernatant containing ATRA during iT$_{reg}$ generation abrogated the loss of Foxp3 expression by A-C/EBP or C/EBPζ, which indicates that methyl-CRE sequence in the Foxp3 CNS2 is critical for C/EBP to regulate Foxp3 expression (FIG. 4E). The importance of the DNA methylation was also confirmed when memory supernatant was replaced with fresh media containing exogenous IFN-γ, IL-4, and IL-2 (FIG. 4F).

Example 6: Attenuation of Resistance Against Inhibitory Cytokines Induced by C/EBβ by RORγT and RORα

Figure 5A:
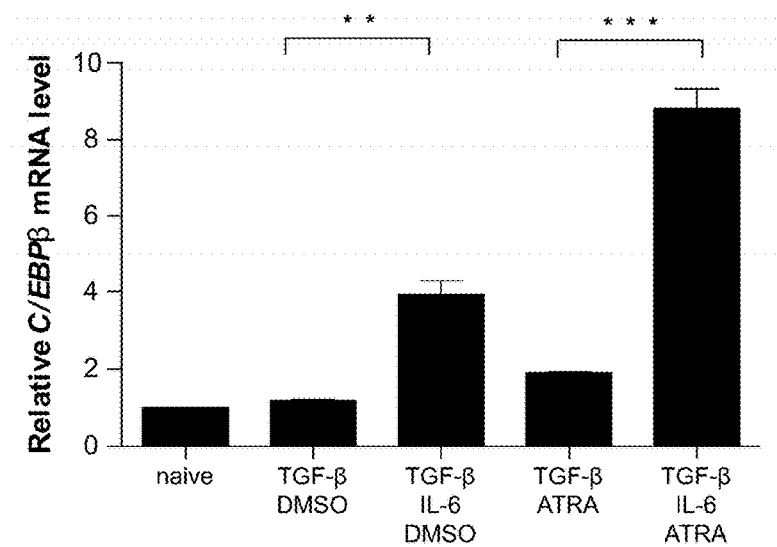
FIGS. 5A-5E represent mutual antagonism between RORγt and C/EBPβ through physical interaction for T$_H$17 differentiation.
Figure 5B:
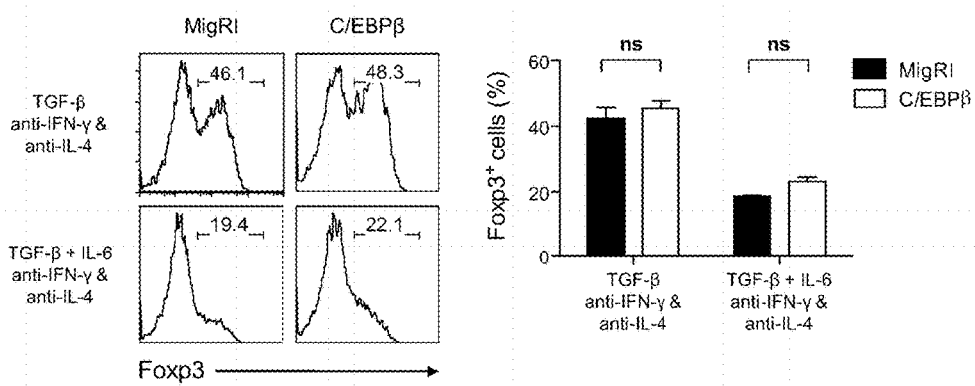
Figure 5C:
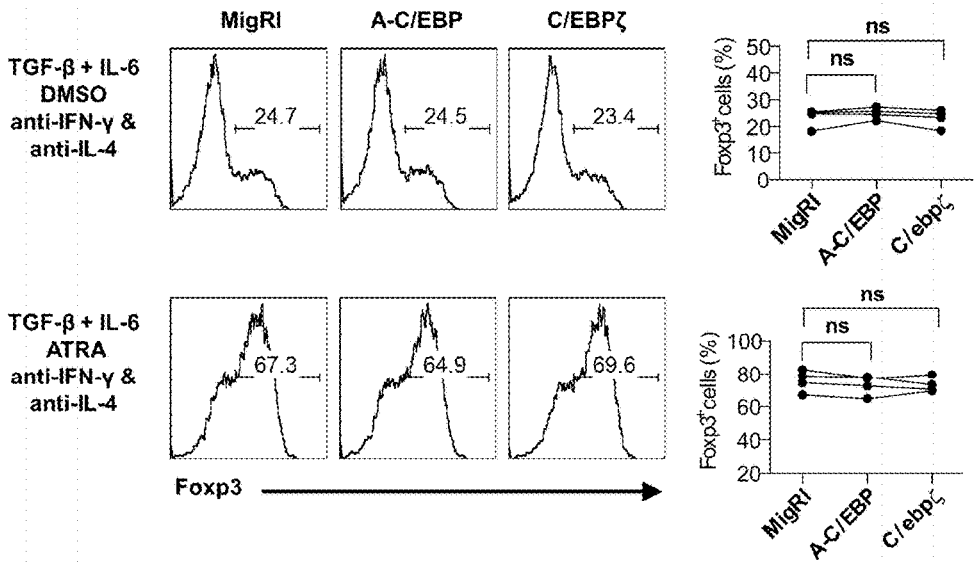
Figure 5D:
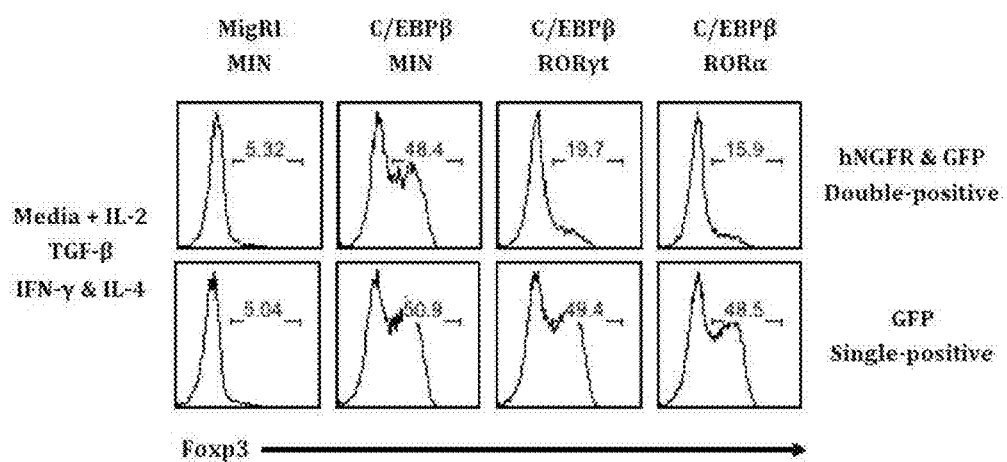
Figure 5E:
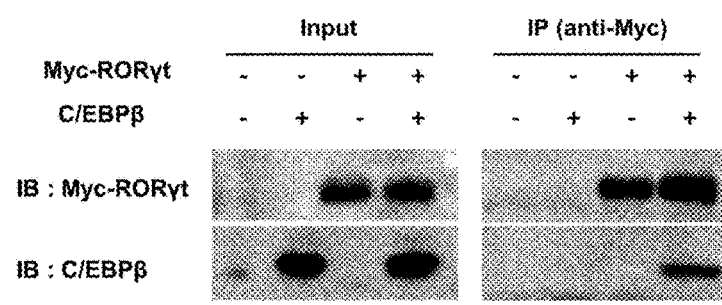

IL-6 suppresses TGF-β-induced Foxp3 expression, which in turn relieves Foxp3-mediated RORγt inhibition, thereby promoting $T_H17$ differentiation (Zhou, L. et al, Nature 453: 236-240, 2008). C/EBPβ has been known as a downstream target of IL-6 (Poli, V. et al., Cell 63: 643-653, 1990). The present inventors observed that the expression of C/EBPβ was increased in CD4+ T cells treated with TGF-β and IL-6 compared with treated only TGF-β (FIG. 5A). Thus, the present inventors investigated whether C/EBP has the ability to overcome IL-β-mediated Foxp3 repression and found that expression of C/EBPβ did not counteract IL-β-mediated Foxp3 repression (FIG. 5B). The present inventors could not find any significant reduction of Foxp3 expression by ectopic expression of A-C/EBP or C/EBPζ in the presence of TGF-β and IL-6 plus ATRA (FIG. 5C). This result suggests that IL-6 signaling may incapacitate the activity of C/EBP from preventing the loss of Foxp3 expression and suppress Foxp3 expression via a C/EBP-independent pathway. RORα inhibits the transcriptional activity of C/EBPβ during adipocyte differentiation through physical association (Ohoka, N. et al., Mol. Endocrinol. 23: 759-771, 2009). Thus the present inventors investigated whether RORγt could block the C/EBPβ-directed resistance to Foxp3 repression. C/EBPβ-directed resistance to Foxp3 repression by memory supernatant during $iT_{reg}$ differentiation was significantly abolished by RORγt expression (FIG. 5D). The present inventors also found that C/EBPβ and RORγt physically interact by co-immunoprecipitation assay (FIG. 5E).

Figure 6A:
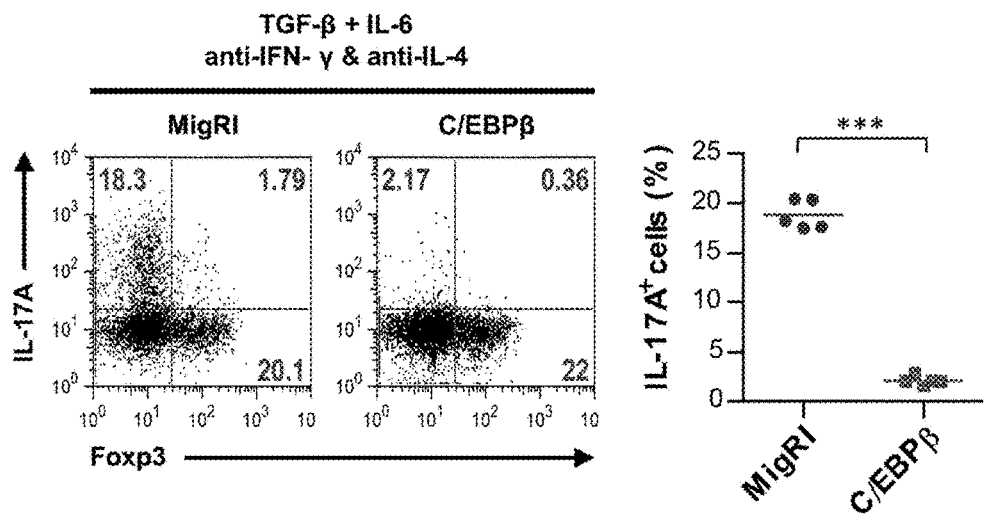
FIGS. 6A-6F represent T$_H$17 expression suppression by C/EBPβ.
Figure 6B:
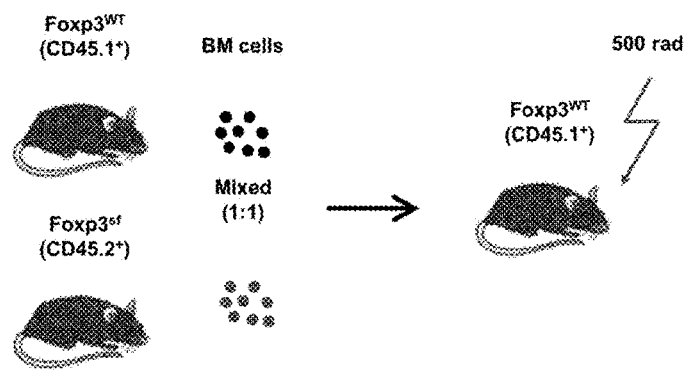
Figure 6C:
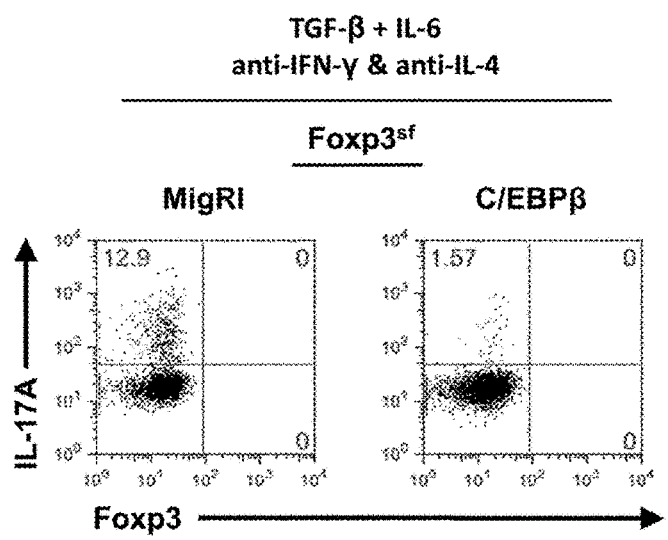
Figure 8A:
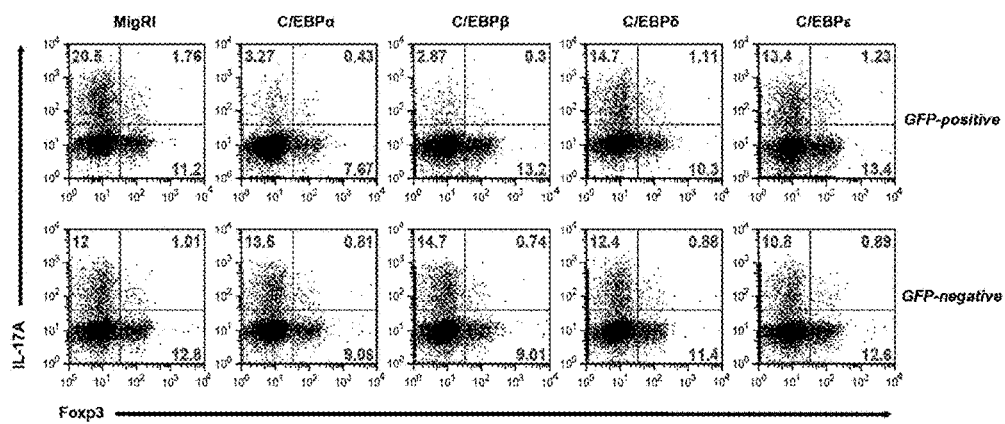
FIGS. 8A-8B represent the repression of $T_H17$ differentiation by C/EBPα, δ and ε.
Figure 8B:
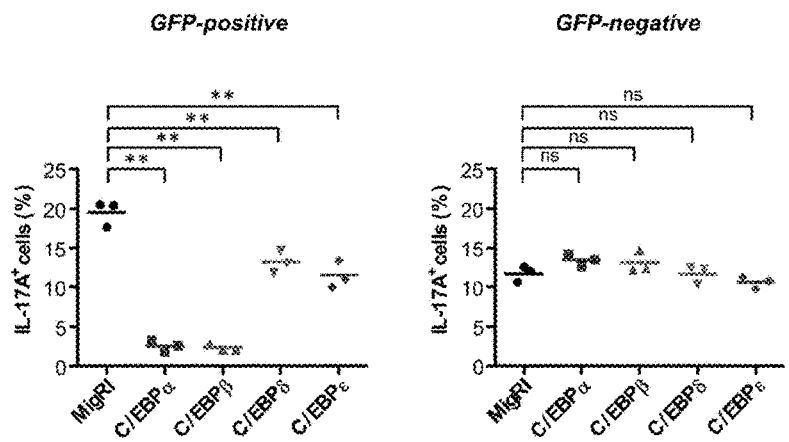

Example 7: Inhibition of $T_H17$ Differentiation by C/EBPβ Due to Disturbing DNA Binding of RORγt Retinoic acid inhibits the IL-β-driven induction of $T_H17$ cells (Mucida, D. et al., Science 317: 256-260, 2007; Xiao, S. et al., J. Immunol. 181, 2277-2284, 2008; Elias, K. M. et al., Blood 111: 1013-1020, 2008). The present inventors thus investigated whether C/EBPβ has a similar antagonistic effect on the $T_H17$ differentiation. As a result, ectopic expression of C/EBPβ drastically reduced $T_H17$ differentiation (FIG. 6A). $T_H17$ was investigated antagonism of C/EBPβ for differentiation. As a result, C/EBPβ expression was shown to significantly inhibit the TH17 differentiation (FIG. 6A). C/EBPα also silenced IL-17A production as much as C/EBPβ, whereas C/EBPδ and C/EBPε repressed it slightly (FIGS. 8A and 8B). In order to formally exclude the possibility that the negative effect of C/EBPβ on $T_H17$ differentiation may result from incomplete IL-β-mediated Foxp3 repression, we employed the scurfy mutant (Foxp3$^{sf}$) mice lacking the forkhead binding domain of Foxp3 (FIG. 6B). Naïve CD4+Foxp3$^{sf}$ T cells were obtained using mixed kimera bone marrow containing scurfy bone marrow (CD45.2+Foxp3$^{sf}$) and congenic wild type bone marrow (CD45.1+Foxp3$^{WT}$) (FIG. 6B). Ectopic expression of C/EBPβ in naïve CD4+Foxp3$^{sf}$ T cells also greatly reduced IL-17A production, indicating that the marginal increase of Foxp3 is not a major factor for C/EBPβ-mediated inhibition of $T_H17$ differentiation and C/EBPβ represses $T_H17$ differentiation through Foxp3-independent pathway (FIG. 6C).

Figure 6D:
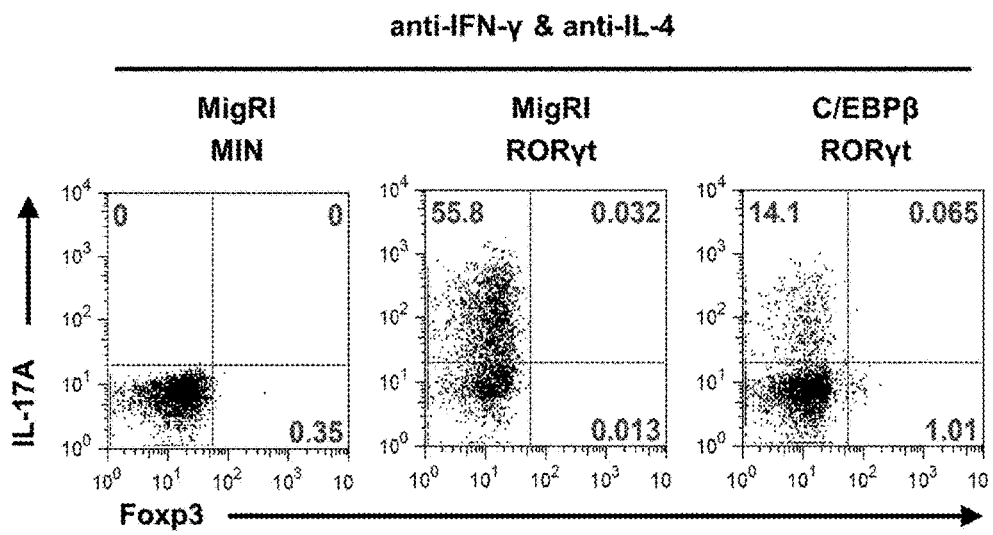
Figure 6E:
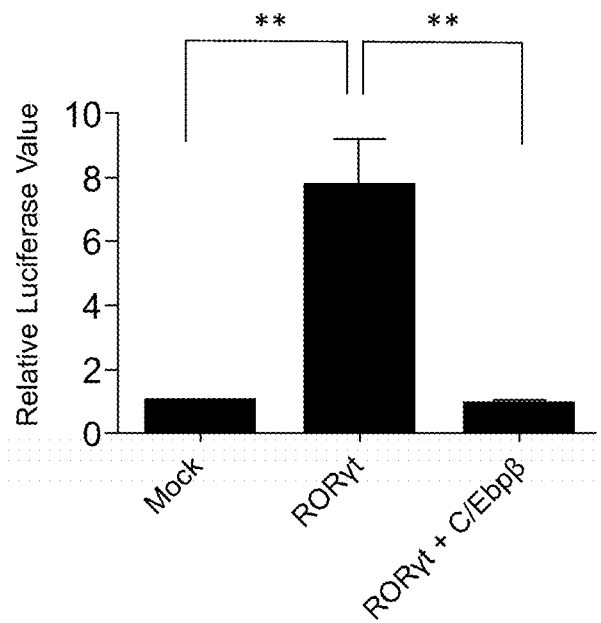

Then the present inventors analyzed gene expression profile related to $T_H17$ by qRT-PCR using GFP+ and GFP− cells illustrated in FIG. 6A, respectively. As a result, compared to control vector-transduced cells, C/EBPβ expression greatly reduced the level of IL-17A and IL-17F mRNA, whereas the level of RORγt and RORα mRNA remained the same. From these results, the present inventors investigated whether C/EBPβ could repress RORγt-mediated IL-17A production, and found that ectopic expression of C/EBPβ in RORγt-transduced cells strikingly diminished RORγt-mediated IL-17A production (FIG. 6D). These results suggest that C/EBPβ may inhibit RORγt activity through physical interaction. In addition, a luciferase reporter assay also showed that transient expression of C/EBPβ could repress the IL-17 promoter-CNS2 reporter activity activated by RORγt (FIG. 6E).

Figure 6F:
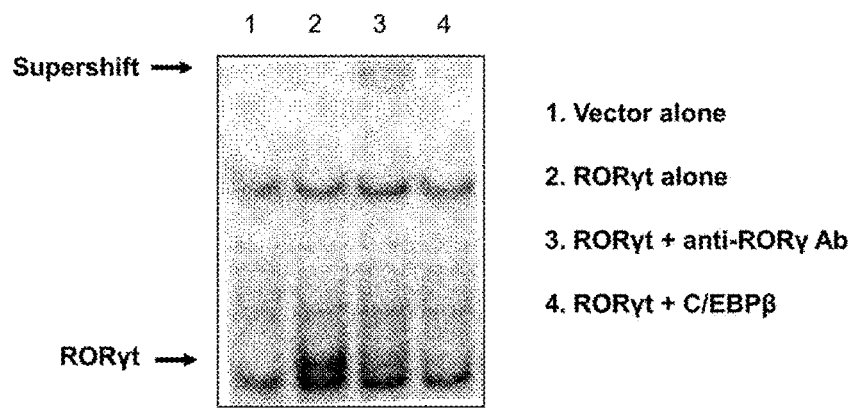

Furthermore, EMSA with a probe corresponding to the putative binding sequences for RORγt indicates that C/EBPβ regulates the binding of RORγt to the IL-17 CNS2 region. RORγt binding to its responsive element was completely abolished by co-expression of C/EBPβ (FIG. 6F). Therefore, C/EBPβ blocks $T_H17$ differentiation by blocking the DNA binding activity of RORγt.

Although exemplary embodiments of the present invention were described in detail as discussed above, the scope of the present invention is not limited thereto and various modification and variations of those skilled in the art using the basic concept of the present invention defined in the following claims belong to the scope of the present invention.

In addition, all technical terms used herein, unless otherwise defined, are commonly understood by those skilled in the art. The contents of all the publications listed in this document are incorporated by reference herein in its entirety.

What is claimed is:

1. An isolated transduced regulatory T cell differentiated from a CD4+ cell selected from the group consisting of a naive T cell, a memory T cell, and an effector T cell, wherein the transduced regulatory T cell is produced by transducing the CD4+ cell with a gene construct comprising a gene encoding C/EBP selected from the group consisting of C/EBPβ, C/EBPγ, and C/EBPδ operably linked to a promoter and treating the transduced CD4+ cell with TGF-β, and wherein the C/EBP is expressed in the transduced CD4+ cell which thereby removes Foxp3 suppression to produce the transduced regulatory T cell which is Foxp3-positive.

2. An isolated stabilized regulatory T cell prepared by transducing a regulatory T cell with a gene construct comprising a gene encoding C/EBP selected from the group consisting of C/EBPβ, C/EBPγ, and C/EBPδ operably linked to a promoter, wherein the C/EBP is expressed in the regulatory T cell, to produce the stabilized regulatory T cell.

3. A composition comprising one or more cells selected from the group consisting of:

an isolated transduced regulatory T cell differentiated from a CD4+ cell selected from the group consisting of a naive T cell, a memory T cell, and an effector T cell, wherein the transduced regulatory T cell is produced by transducing the CD4+ cell with a gene construct comprising a gene encoding C/EBP selected from the group consisting of C/EBPβ, C/EBPγ, and C/EBPδ operably linked to a promoter and treating the transduced CD4+ cell with TGF-β wherein the C/EBP is expressed in the transduced CD4+ cell which thereby removes Foxp3 suppression to produce the transduced regulatory T cell which is Foxp3-positive; and an isolated stabilized regulatory T cell prepared by transducing a regulatory T cell with a gene construct comprising the gene encoding C/EBP operably linked to a promoter and wherein the C/EBP is expressed in the regulatory T cell to produce the isolated stabilized regulatory T cell.

4. An in vitro method of differentiating an isolated CD4+ cell selected from the group consisting of a naive T cell, a memory T cell, and an effector T cell into an induced regulatory T cell, the method comprising:

delivering C/EBP selected from the group consisting of C/EBPβ, C/EBPγ, and C/EBPδ to the nucleus of the CD4+ cell wherein the C/EBP is in a form of a fusion protein linked to a cell penetrating peptide or is formulated with cationic lipids and treating the CD4+ cell comprising the C/EBP with TGF-β; or transducing the CD4+ cell with a gene construct comprising a polynucleotide encoding the C/EBP operably linked to a promoter and wherein the C/EBP is expressed in the CD4+ cell and treating the CD4+ cell comprising the C/EBP with TGF-β wherein the treated CD4+ cell comprising the C/EBP differentiates into the induced regulatory T cell.

5. An in vitro method of stabilizing an isolated regulatory T cell, the method comprising:

delivering C/EBP selected from the group consisting of C/EBPβ, C/EBPγ, and C/EBPδ to the nucleus of the regulatory T cell wherein the C/EBP is in a form of fusion protein linked to a cell penetrating peptide or is formulated with cationic lipids; or transducing the regulatory T cell with a gene construct comprising a polynucleotide encoding the C/EBP operably linked to a promoter wherein the C/EBP is expressed in the regulatory T cell wherein the regulatory T cell comprising the C/EBP is the stabilized regulatory T cell.

6. An in vitro method of inhibiting differentiation of an isolated CD4+ cell selected from the group consisting of a naive T cell, a memory T cell, and an effector T cell into a TH17 cell, the method comprising:

delivering C/EBP selected from the group consisting of C/EBPβ, C/EBPγ, and C/EBPγ to the nucleus of the CD4+ cell wherein the C/EBP is in a form of fusion protein linked to a cell penetrating peptide or is formulated with cationic lipids in the presence of and treating the CD4+ cell with TGF-B; or transducing the CD4+ cell with a gene construct comprising a polynucleotide encoding the C/EBP operably linked to a promoter and wherein the C/EBP is expressed in the CD4+ cell- and treating the transduced CD4+ cell with TGF-β wherein the treated CD4+ cell comprising the C/EBP does not differentiate into the TH17 cell.

* * * * *

SEQUENCE LISTING

<160> NUMBER OF SEQ ID NOS: 17

<210> SEQ ID NO 1
<211> LENGTH: 19
<212> TYPE: DNA
<213> ORGANISM: Artificial Sequence
<220> FEATURE:
<223> OTHER INFORMATION: C/EBP beta forward

<400> SEQUENCE: 1
agcggctgca gaagaaggt                                                  19

<210> SEQ ID NO 2
<211> LENGTH: 21
<212> TYPE: DNA

```
<213> ORGANISM: Artificial Sequence
<220> FEATURE:
<223> OTHER INFORMATION: C/EBP beta reverse

<400> SEQUENCE: 2
ggcagctgct tgaacaagtt c                                              21

<210> SEQ ID NO 3
<211> LENGTH: 21
<212> TYPE: DNA
<213> ORGANISM: Artificial Sequence
<220> FEATURE:
<223> OTHER INFORMATION: Foxp3 forward

<400> SEQUENCE: 3
ggacagacca cacttcatgc a                                              21

<210> SEQ ID NO 4
<211> LENGTH: 20
<212> TYPE: DNA
<213> ORGANISM: Artificial Sequence
<220> FEATURE:
<223> OTHER INFORMATION: Foxp3 reverse

<400> SEQUENCE: 4
gctgatcatg gctgggttgt                                                20

<210> SEQ ID NO 5
<211> LENGTH: 18
<212> TYPE: DNA
<213> ORGANISM: Artificial Sequence
<220> FEATURE:
<223> OTHER INFORMATION: beta-actin forward

<400> SEQUENCE: 5
caacgagcgg ttccgatg                                                  18

<210> SEQ ID NO 6
<211> LENGTH: 20
<212> TYPE: DNA
<213> ORGANISM: Artificial Sequence
<220> FEATURE:
<223> OTHER INFORMATION: beta-actin reverse

<400> SEQUENCE: 6
gccacaggat tccataccca                                                20

<210> SEQ ID NO 7
<211> LENGTH: 19
<212> TYPE: DNA
<213> ORGANISM: Artificial Sequence
<220> FEATURE:
<223> OTHER INFORMATION: Foxp3 TDSR forward

<400> SEQUENCE: 7
cctccttgtt gccgatgaa                                                 19

<210> SEQ ID NO 8
<211> LENGTH: 22
<212> TYPE: DNA
<213> ORGANISM: Artificial Sequence
<220> FEATURE:
<223> OTHER INFORMATION: Foxp3 TDSR reverse

<400> SEQUENCE: 8
cacaacctga acttggccag at                                             22
```

<210> SEQ ID NO 9
<211> LENGTH: 25
<212> TYPE: DNA
<213> ORGANISM: Artificial Sequence
<220> FEATURE:
<223> OTHER INFORMATION: Foxp3 TDSR forward

<400> SEQUENCE: 9
ttttgggttt tttggtatt taaga                                  25

<210> SEQ ID NO 10
<211> LENGTH: 25
<212> TYPE: DNA
<213> ORGANISM: Artificial Sequence
<220> FEATURE:
<223> OTHER INFORMATION: Foxp3 TDSR reverse

<400> SEQUENCE: 10
ttaaccaaat ttttctacca ttaac                                 25

<210> SEQ ID NO 11
<211> LENGTH: 28
<212> TYPE: DNA
<213> ORGANISM: Artificial Sequence
<220> FEATURE:
<223> OTHER INFORMATION: Foxp3 TSDR methyl-CRE forward
<220> FEATURE:
<221> NAME/KEY: variation
<222> LOCATION: (14)
<223> OTHER INFORMATION: methylated

<400> SEQUENCE: 11
ccggccgcca tgacgtcaat ggcagaaa                              28

<210> SEQ ID NO 12
<211> LENGTH: 28
<212> TYPE: DNA
<213> ORGANISM: Artificial Sequence
<220> FEATURE:
<223> OTHER INFORMATION: Foxp3 TSDR methyl-CRE reverse
<220> FEATURE:
<221> NAME/KEY: variation
<222> LOCATION: (14)
<223> OTHER INFORMATION: methylated

<400> SEQUENCE: 12
tttctgccat tgacgtcatg gcggccgg                              28

<210> SEQ ID NO 13
<211> LENGTH: 28
<212> TYPE: DNA
<213> ORGANISM: Artificial Sequence
<220> FEATURE:
<223> OTHER INFORMATION: Foxp3 TSDR unmethyl-CRE forward

<400> SEQUENCE: 13
ccggccgcca tgacgtcaat ggcagaaa                              28

<210> SEQ ID NO 14
<211> LENGTH: 28
<212> TYPE: DNA
<213> ORGANISM: Artificial Sequence
<220> FEATURE:
<223> OTHER INFORMATION: Foxp3 TSDR unmethyl-CRE reverse

<400> SEQUENCE: 14

```
tttctgccat tgacgtcatg gcggccgg                                           28

<210> SEQ ID NO 15
<211> LENGTH: 31
<212> TYPE: DNA
<213> ORGANISM: Artificial Sequence
<220> FEATURE:
<223> OTHER INFORMATION: ROR element in IL17 CNS2 forward

<400> SEQUENCE: 15
gaaagttttc tgacccactt taaatcaatt t                                       31

<210> SEQ ID NO 16
<211> LENGTH: 31
<212> TYPE: DNA
<213> ORGANISM: Artificial Sequence
<220> FEATURE:
<223> OTHER INFORMATION: ROR element in IL17 CNS2 reverse

<400> SEQUENCE: 16
aaattgattt aaagtgggtc agaaaacttt c                                       31

<210> SEQ ID NO 17
<211> LENGTH: 8
<212> TYPE: DNA
<213> ORGANISM: Artificial Sequence
<220> FEATURE:
<223> OTHER INFORMATION: methylated CRE sequence
<220> FEATURE:
<221> NAME/KEY: variation
<222> LOCATION: (4)
<223> OTHER INFORMATION: methylated

<400> SEQUENCE: 17 tgacgtca                                                                 8
```